United States Patent
Mckinney et al.

(10) Patent No.: US 9,758,773 B2
(45) Date of Patent: Sep. 12, 2017

(54) THERMOSTABLE TYPE-A DNA POLYMERASE MUTANT WITH INCREASED RESISTANCE TO INHIBITORS IN BLOOD

(71) Applicant: Agilent Technologies, Inc., Loveland, CO (US)

(72) Inventors: Nancy Mckinney, La Jolla, CA (US); Holly H. Hogrefe, San Diego, CA (US); Jeffrey Fox, Escondido, CA (US); Connie J. Hansen, San Diego, CA (US); Bahram Arezi, Carlsbad, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 116 days.

(21) Appl. No.: 14/568,549

(22) Filed: Dec. 12, 2014

(65) Prior Publication Data
US 2015/0232821 A1 Aug. 20, 2015

Related U.S. Application Data

(60) Provisional application No. 61/940,172, filed on Feb. 14, 2014.

(51) Int. Cl.
*C12N 9/12* (2006.01)
*C12Q 1/68* (2006.01)

(52) U.S. Cl.
CPC .......... *C12N 9/1252* (2013.01); *C12Q 1/686* (2013.01); *C12Y 207/07007* (2013.01)

(58) Field of Classification Search
CPC .................. C12N 9/1252; C12Q 1/686; C12Y 207/07007
See application file for complete search history.

(56) References Cited

U.S. PATENT DOCUMENTS

2011/0027833 A1 2/2011 Hogrefe et al.
2012/0053062 A1 3/2012 Brooks

FOREIGN PATENT DOCUMENTS

| WO | WO2010062777 A2 | 6/2010 |
|----|----|----|
| WO | 2011014885 A1 | 2/2011 |
| WO | WO2011014885 | 2/2011 |
| WO | WO2012097318 | 7/2012 |

OTHER PUBLICATIONS

Ma, Wu-Po et al., "RNA template-dependent 5' nuclease activity of Thermus aquaticus and Thermus thermophiles DNA polymerases" *Journal of Biological Chem, American Society for Biochemistry and Molecular Biology*, US. vol. 275, No. 32, pp. 24693-24700, Aug. 11, 2000.

Yokota, Masaharu et al., "Effects of heparin on polymerase chain reaction for blood white cells", *Journal of Clinical Laboratory Analysis*, vol. 13, No. 3, pp. 133-140, 1999.

Alba, M. Mar, "Replicative DNA Polymerases," Genome Biology (2001):2(10):reviews3002.1-3002.4.

Steitz, Thomas A., "DNA Polymerases: Structural Diversity and Common Mechanisms," J. Biol. Chem. (1999): 274:17395-17398.

(Continued)

*Primary Examiner* — Alexander Kim

(57) ABSTRACT

The invention provides mutants of DNA polymerases having an enhanced resistance to inhibitors of DNA polymerase activity. The mutant polymerases are well suited for PCR amplification of targets in samples that contain inhibitors of wild-type polymerases.

14 Claims, 9 Drawing Sheets

(56) References Cited

OTHER PUBLICATIONS

Filee et al., "Evolution of DNA Polymerase Families: Evidences for Multiple Gene Exchange Between Cellular and Viral Proteins," J. mol. Evol. (2002): 54:763-773.
Garcia et al., "Anticoagulants Interfere with PCR Used to Diagnose Invasive Aspergillosis," J. CLin. Microbiol. (2002): 40(4):1567-1568.

Figure 1

```
CLUSTAL 2.0.10 multiple sequence alignment

Thermus.Thermophilus.HB8         MEAMLPLFEPKGRVLLVDGHHLAYRTFFALKG-LTTSRGEPVQAVYGFAK  49
Thermus.caldophilus              MEAMLPLFEPKGRVLLVDGHHLAYRTFFALKG-LTTSRGEPVQAVYGFAK  49
Thermus.thermophilus.HB27        MEAMLPLFESKGRVLLVDGHHLAYRTFFALKG-LTTSRGEPVQAVYGFAK  49
Thermus.aquaticus                HPGMLPLFEPKGRVLLVDGHHLAYRTFHALKG-LTTSRGEPVQAVYGFAK  49
Thermus.scotoductus              KRAMLPLFEPKGRVLLVDGHHLAYRIFFALKG-LTTSRGEPVQAVYGFAK  49
Thermus.flavus                   -MAMLPLFEPKGRVLLVDGHHLAYRTFFALKG-LTTSRGEPVQAVYGFAK  48
Thermus.oshimai                  ---MLPLFEPKGRVLLVDGHHLAYRTFFALKG-LTTSRGEPVQAVYGFAK  46
Thermus.filiformis               MTPLFDLEEPPKRVLLVDGHHLAYRTFYALS--LTTSRGEPVQMVYGFAR  48
Thermotoga.maritima.MSB8         ----------MARLFLFDGTALAYRAYYALDRSLSTSTGIPTNAYYGVAR  40
Thermotoga.neapolitana.DSM4359   ----------MARLFLFDGTALAYRAYYALDRSLSTSTGIPTNAYYGVAR  40
                                           *::*.**  ****::.**.  *:** * *.: .*..*:

Thermus.Thermophilus.HB8         SLLKALKEDGY----KAVFVVFDAKAPSFRHEAYEAYKAGRAPTPEDFPRQ  96
Thermus.caldophilus              SLLKALKEDGY----KAVFVVFDAKAPSFRHEAYEAYKAGRAPTPEDFPRQ  96
Thermus.thermophilus.HB27        SLLKALKEDGY----KSVFVVFDAKAPSFRHEAYEAYKAGRAPTPEDFPRQ  96
Thermus.aquaticus                SLLKALKEDG-----DAVIVVFDAKAPSFRHEAYGGYKAGRAPTPEDFPRQ  95
Thermus.scotoductus              SLLKALPEDG-----DVVIVVFDAKAPSFRHQTYEAYKAGRAPTPEDFPRQ  95
Thermus.flavus                   SLLKALKEDG-----DVVVVVFDAKAPSFRHEAYEAYKAGRAPTPEDFPRQ  94
Thermus.oshimai                  SLLKALKEDG-----EVAIVVFDAKAPSFRHEAYEAYKAGRAPTPEDFPRQ  92
Thermus.filiformis               SLLKALKEDG-----QAVVVVFDAKAPSFRHEAYEAYKAGRAPTPEDFPRQ  94
Thermotoga.maritima.MSB8         MLVRFIRDHIIVGKDYVAVAFDKKAATFRHKLLETTRAQRPKTPDLLIGQ  90
Thermotoga.neapolitana.DSM4359   MLVKFIKEHIIPEKDYAAVAFDKKAATFRHKLLEAYKAQRPKTPDLLVGQ  90
                                 *::   :::.       . .*.** **.:***:    *** *. **: :.*

Thermus.Thermophilus.HB8         LALIKELVDLLGFTRLEVPGYEADDVLATLAKKAEKEGYEVRILTADRDL  146
Thermus.caldophilus              LALIKELVDLLGFTRLEVPGYEADDVLATLAKNPEKEGYEVRILTADRDL  146
Thermus.thermophilus.HB27        LALIKELVDLLGFTRLEVPGYEADDVLATLAKKAEKEGYEVRILTADRDL  146
Thermus.aquaticus                LALIKELVDLLGLARLEVPGYEADDVLASLAKKAEKEGYEVRILTADRDL  145
Thermus.scotoductus              LALIKEMVDLLGLERLEVPGFEADDVLATLAKKAEKEGYEVRILTADRDL  145
Thermus.flavus                   LALIKELVDLGLVRLEVPGFEADDVLATLAKRAEKEGYEVRILTADRDL  144
Thermus.oshimai                  LALIKELVDLLGLVRLEVPGFEADDVLATLAKKAEPEGYEVRILSADRDL  142
Thermus.filiformis               LALVKRLVDLLGLVRLEAPGYEADDVLGTLAKKAEREGMEVPILTGDRDF  144
Thermotoga.maritima.MSB8         LPYIKKLVEALGMKVLEVEGYEADDIIATLAVKGLPLFDEIFIVTGDKDM  140
Thermotoga.neapolitana.DSM4359   LPYIKRLIEALGFKVLELEGYEADDIIATLAVKGCTFFDEIFIITGDKDM  140
                                 *. :*.::: **:   **  ****::.** .       *: *::.*:*:

Thermus.Thermophilus.HB8         YQLVSDRVAVLHPEG--------HLITPEWLWEKYGLRPEQWVDFRALVGDPS  191
Thermus.caldophilus              DQLVSDRVAVLHPEG--------HLITPEWLWQKYGLKPEQWVDFRALVGDPS  191
Thermus.thermophilus.HB27        YQLVSDRVAVLHPEG--------HLITPEWLWEKYGLRPEQWVDFRALVGDPS  191
Thermus.aquaticus                YQLLSDRIHVLHPEG--------YLITPAWLWEKYGLRPDQWADYRALTGDES  190
Thermus.scotoductus              YQLLSERISILHPEG--------YLITPEWLWEKYGLKPSQWVDYRALAGDPS  190
Thermus.flavus                   YQLLSEPIAILHPEG--------YLITPAWLYEKYGLRPEQWVDYRALAGDPS  189
Thermus.oshimai                  YQLLSDRIHLLHPEG--------EVLTPGWLQERYGLSPERWVEYRALVGDPS  187
Thermus.filiformis               FQLLSEKVSVLLPDG--------TLVTPKDVQEKYGVPPERWVDFRALTGDRS  189
Thermotoga.maritima.MSB8         LQLVNEKIKVWRIVKGISDLELYDAQKVHEKYGVEPQQIPDLLALTGDEI  190
Thermotoga.neapolitana.DSM4359   LQLVNEKIKVWRIVKGISDLELYDSKKVKERYGVEPHQIPDLLALTGDEI  190
                                 **::::: :                :  :**:  *  *  **.**
```

Figure 1 (cont.)

```
Thermus.Thermophilus.HB8        DNLPGVKGIGEKTALKLLKEWGSLENLLKNLDRVKPENVREKIKAHLEDL 241
Thermus.caldophilus             DNLPGVKGIGEKTALKLLKEWGSLENLLKNLDRVKPENVREKIKAHLEDL 241
Thermus.thermophilus.HB27       DNLPGVKGIGEKTALKLLKEWGSLESLLKNLDRVKPENVREKIKAHLEDL 241
Thermus.aquaticus               DNLPGVKGIGEKTASKLLEEWGSLEALLKNLDRLKP-AIPEKILAHMEDL 239
Thermus.scotoductus             DNIPGVRGIGEKTAAKLIREWGSLENLLEHLEQVKPASVREKILSHREDL 240
Thermus.flavus                  DNIPGVKGIGEKTAQRLIPEWGSLEMLFQHLDQVKPS-LPEKLQAGMEAL 238
Thermus.oshimai                 DNLPGVPGIGEKTALKLLKEWGSLEAILKNLDQVKPERVREAIRNNLDKL 237
Thermus.filiformis              DNIPGVAGIGEKTALPLLAEWGSVENLLKNLDRVKPDSVPPKIEAHLEDL 239
Thermotoga.maritima.MSB8        DNIPGVTGIGEKTAVQLLEKYKDLEDILNHVR-ELPQKVRKALLRDPENA 239
Thermotoga.neapolitana.DSM4359  DNIPGVTGIGEKTAVQLLGPYPNLEDILEHAR-ELPQRVPKALLRDREVA 239
                                 *:*** ******* :*: :: ::* ::::     * :*: :      :

Thermus.Thermophilus.HB8        PLSLELSRVRTDLPLEVDLA---QGPEPDREGLRAFLERLEFGSLLHEFGL 289
Thermus.caldophilus             RLSLELSPVPTDLPLEVDLA---QGREPDREGLPAFLERLEFGSLLHEFGL 289
Thermus.thermophilus.HB27       PLSLELSRVRADLPLEVDLA---QGREPDREGLRAFLERLEFGSLLHEFGL 289
Thermus.aquaticus               KLSWDLAKVRTDLPLEVDFA---KRREPDPERLRAFLERLEFGSLLHEFGL 287
Thermus.scotoductus             KLSLELSRVRTDLPLEVDFA---PRREPDREGLKAFLERLEFGSLLHEFGL 288
Thermus.flavus                  ALSPKLSQVRTDLPLEVDFG---RRRTPNLEGLRAFLERLEFGSLLHEFGL 286
Thermus.oshimai                 QNSLELSRLRTDLPLEVDFA---KRREPDWEGLKAFLERLEFGSLLHEFGL 285
Thermus.filiformis              RLSLDLARIRTDLPLEVDFKALPRRTPDLEGLRAFLEELEFGSLLHEFGL 289
Thermotoga.maritima.MSB8        ILSKKLAILETNVPIEINWEELRYQGYDREKLLPLLKELEFASIKKELQL 289
Thermotoga.neapolitana.DSM4359  ILSKKLATLVTNAFVEVDWEEMKYPGYDKRKLLPILKELEFASINKELQL 289
                                 :* .*: : :: *::::      : :  :: *. :*:.***.*:::*: *

Thermus.Thermophilus.HB8        LEAPAPL-----------EEAPWPPPE---GAFVGFVLSRPEPMWAELKAL 326
Thermus.caldophilus             LEAPAPL-----------EEAPWPPPE---GAFVGFVLSPPEPMWAELKAL 326
Thermus.thermophilus.HB27       LEAPTPL-----------EEAPWPPPE---GAFVGFVLSRPEPMWAELKAL 326
Thermus.aquaticus               LESPKAL-----------EEAPWPPPE---GAFVGFVLSRKEPMWAELLAL 324
Thermus.scotoductus             LESPVAA-----------EEAPWPPPE---GAFVGYVLSRPEPMWAELMAL 325
Thermus.flavus                  LEGPKAA-----------EEAPWPPPE---GAFLGFSFSRPEPMWAELLAL 323
Thermus.oshimai                 LEAPKEA-----------EEAPWPPPG---GAFLGFLLSPPEPMWAELLAL 322
Thermus.filiformis              LGGEKPR-----------EEAPWPPPE---GAFVGFLLSRKEPMWAELLAL 326
Thermotoga.maritima.MSB8        YEESEPVGYRIVKDLVEFEKLIEKLRESPSPAIDLETSSLDPFDCPIVGI 339
Thermotoga.neapolitana.DSM4359  YEEAEPTGYEIVKDHKTFEDLIEKLKEVPSFALDLETSSLDPFNCEIVGI 339
                                  *.      .:  :.   * :*:  ::  ::

Thermus.Thermophilus.HB8        AACRDGR----------VHPAADPLAGLKDLKEVRGLLAK------------D 357
Thermus.caldophilus             AACPDGR----------VHRAADPLAGLPDLKEVRGLLAK------------D 357
Thermus.thermophilus.HB27       AACRDGR----------VHPAEDPLAGLGDLEEVRGLLAK------------D 357
Thermus.aquaticus               AAARGGR----------VHRAPEPYKALRDLKEARGLLAK------------D 355
Thermus.scotoductus             AAAWEGR----------VYRAEDPLEALRGLGEVPGLLAK------------D 356
Thermus.flavus                  AGAWEGR----------LHPAQDPLRGLRDLKGVRGILAK------------D 354
Thermus.oshimai                 AGAKEGP----------VKRAEDPVGALEDLPEIRGLLAK------------D 353
Thermus.filiformis              AAAAEGR----------VHPATSPYEALADLKEARGFLAK------------D 357
Thermotoga.maritima.MSB8        SVSFKPKEAYYIPLHERNAQNLDEKFVLKKLKEILEDPGAKIVGQNLKFD 389
Thermotoga.neapolitana.DSM4359  SVSFKPKTAYYIPLHMPNAQNLDETLVLSKLKEILEDPSSKIVGQNLKYD 389
                                 :  :        :*  .  :    *   :*.      :
```

Figure 1 (cont.)

```
Thermus.Thermophilus.HB8          LAVLASREGLDLVPGDDPMLLAYLLDPS--NTTPEGVARRYGG--------  398
Thermus.caldophilus               LAVLASREGLDLVPGDDPMLLAYLLDPS--NTTPEGVAPRYGG--------  398
Thermus.thermophilus.HB27         LAVLALREGLDLAPGDDPMLLAYLLDPS--NTTPEGVARRYGG--------  398
Thermus.aquaticus                 LSVLALREGLGLPPGDDPMLLAYLLDPS--NTTPEGVARRYGG--------  396
Thermus.scotoductus               LAVLALREGIALAPGDDPMLLAYLLDPS--NTAPEGVAPRYGG--------  397
Thermus.flavus                    LAVLALREGLDLFPEDDPMLLAYLLDPS--NTTPEGVARRYGG--------  395
Thermus.oshimai                   LSVLALREGREIPPGDDPMLLAYLLDPG--NTNPEGVARRYGG--------  394
Thermus.filiformis                LAVLALREGVALDPTDDPLLVAYLLDPA--NTNPEGVAPRYGG--------  398
Thermotoga.maritima.MSB8          YKVLHVEGVEPVPPYFDTNIAAVLLEPNEKKFNLDDLALKFLGYKNTSYQ  439
Thermotoga.neapolitana.DSM4359    YKVLHVKGISPVYPHFDTNIAAYLLEPNEKKFNLEDLSLRFLGYKNTSYQ  439
                                   **  :    : *  *.:: ****;*    (   ).:: :: *

Thermus.Thermophilus.HB8          -------------------------EWTEDAAHRALLSERLHRNLLPRLEGEEKL  428
Thermus.caldophilus               -------------------------EWTEDAAHRALLSERLHRNLLKRLQGEERL  428
Thermus.thermophilus.HB27         -------------------------EWTEDAAHRALLSERLHPNLLKRLEGEEKL  428
Thermus.aquaticus                 -------------------------EWTEEAGERAALSERLFANLNGRLEGEERL  426
Thermus.scotoductus               -------------------------EWTEEAGERALLSERLYAALLERLKGEERL  427
Thermus.flavus                    -------------------------EWTEDAGERALLAERLFQTLKERLKGEERL  425
Thermus.oshimai                   -------------------------EWREDAAARALLSERLWQALYPRVAEEERL  424
Thermus.filiformis                -------------------------EFTEDAAEPALLSERLFQNLFPRLS--EKL  426
Thermotoga.maritima.MSB8          ELMSFSPPLFGFSFADVPVEKAANYSCEDADITYRLYKTLSLRLH-EADL        488
Thermotoga.neapolitana.DSM4359    ELMSFSSPLFGFSFADVPVDKAANYSCEDADITYRLYKILSMKLH-EAEL        486
                                    :  :   *  :: **     *   ::          *

Thermus.Thermophilus.HB8          LWLYHEVEKPLSRVLAHMEATGVRLDVAYLQALSLELAEEIRRLEEEVFR  478
Thermus.caldophilus               LWLYHEVEKPLSRVLAHMEATGVRLDVAYLQALSLELAEEIRRLEEEVFR  478
Thermus.thermophilus.HB27         LWLYHEVEKPLSRVLAHMEATGVRLDVAYLQALSLELAEEIRRLEEEVFR  478
Thermus.aquaticus                 LWLYPEVERPLSAVLAHMEATGVRLDVAYLPALSLEVAEEIARLEAEVFR  476
Thermus.scotoductus               LWLYEEVEKPLSRVLAHMEATGVRLDVAYLKALSLEVEAELPRLEEEVHR  477
Thermus.flavus                    LWLYEEVERPLSRVLAHMEATGVRLDVAYLQALSLEVEAEVRGLEEEVFR  475
Thermus.oshimai                   LWLYREVERPLAQVLAHMEATGVRLDVPYLEALSQEVAFELERLEAEVHR  474
Thermus.filiformis                LULYQEVERPLSRVLAHMEARGVRLDVPLLEALSFELERMERLEGEVFR  476
Thermotoga.maritima.MSB8          ENVFYKIENPLVNVLAKMELNGVYVDTEFLKRLSEEYGKKLEELAEEIYS  538
Thermotoga.neapolitana.DSM4359    ENVFYRIEMPLVNVLARMELNGVYVDTEFLKKLSEEYGKKLEELAEKIYQ  538
                                   : ;.:* **  ***;**  ** :*.  *;. ** *   :: .* :):.;

Thermus.Thermophilus.HB8          LAGHPFNLNSRDQLERVLFDELRLPALGKTQKTGKRSTSAAVLEALREAH  528
Thermus.caldophilus               LAGHPFNLNSRDQLERVLFDELRLPALGKTQKTGKRSTSAAVLEALREAH  528
Thermus.thermophilus.HB27         LAGHPFNLNSRDQLERVLFDELRLPALGKTQKTGKRSTSAAVLEALREAH  528
Thermus.aquaticus                 LAGHPFNLNSRDQLERVLFDELGLPAIGKTEKTGKRSTSAAVLEALREAH  526
Thermus.scotoductus               LAGHPFNLNSRDQLEPVLFDELGLPAIGKTEKTGKRSTSAAVLEALREAH  527
Thermus.flavus                    LAGHPFNLNSRDQLERVLFDELGLPAIGKTEKTGKRSTSAAVLEALREAH  525
Thermus.oshimai                   LAGHPFNLNSRDQLERVLFDELGLPIGKTEKTGKRSTSAAVLELLREAH  524
Thermus.filiformis                LAGHPFNLNSRDQLEPVLFDELGLTPVGRTEKTGKRSTAQGALEALRGAH  526
Thermotoga.maritima.MSB8          IAGEPFNINSPKQVSRILFEKLGIKRPGKTTKTGDYSTRIEVLEELAGEH  586
Thermotoga.neapolitana.DSM4359    IAGEPFNINSPKQVSRILFEKLGIKPRGKTTKTGEYSTRIEVLEEIAMEH  588
                                   :** ****;**  .*;.::*::;*  : . *:* ***. **  .**  ;    *
```

Figure 1 (cont.)

```
Thermus.Thermophilus.HB8        PIVEKILQHRELTKLKNTYVDPLPSLVHPRTGRLHTRFNQTATATGRLSS  578
Thermus.caldophilus             PIVEKILQHRELTKLKNTYVDPLPSLVHPNTGRLHTRFNQTATATGRLSS  578
Thermus.thermophilus.HB27       PIVEKILQHRELTKLKNTYVDPLPSLVHPRTGRLHTRFNQTATATGRLSS  578
Thermus.aquaticus               PIVEKILQYRELTKLKSTYIDPLPDLIHPRTGRLHTRFNQTATATGRLSS  576
Thermus.scotoductus             PIVDRILQYRELSKLKGTYIDPLPALVHPKTNRLHTRFNQTATATGRLSS  577
Thermus.flavus                  PIVDPILQYRELTKLKNTYIDPLPALVHPKTGRLHTRFNQTATATGRLSS  575
Thermus.oshimai                 PIVGRILEYRELMKLKSTYIDPLPRLVHPKTGRLHTRFNQTATATGRLSS  574
Thermus.filiformis              PIVELILQYRELSKLKSTYLDPLPRLVHPKTGRLHTRFNQTATATGRLSS  576
Thermotoga.maritima.MSB8        EIIPLILEYPKIQKLKSTYIDALPKMVNPKTGRIHASFNQTGTATGRLSS  638
Thermotoga.neapolitana.DSM4359  EIVPLILEYPKIQKLKSTYIDTLPKLVNPKTGRIHASFHQTGTATGRLSS  638
                                *:  **::*:: ***.**:*.** :::*.*.*:*: *:**.********

Thermus.Thermophilus.HB8        SDPNLQNIPVRTPLGQRIRRAFVAEAG-WALVALDYSQIELRVLAHLSGD  627
Thermus.caldophilus             SDPNLQNIPVRTPLGQRIRRAFVAEAG-WALVALDYSQIELRVLAHLSGD  627
Thermus.thermophilus.HB27       SDPNLQNIPVRTPLGQRIRRAFVAEAG-WALVALDYSQIELRVLAHLSGD  627
Thermus.aquaticus               SDPNLQNIPVRTPLGQRIRRAFIAEEG-WLLVALDYSQIELRVLAHLSGD  625
Thermus.scotoductus             SDPNLQNIPVRTPLGQRIRRAFVAEEG-WRLVVLDYSQIELRVLAHLSGD  626
Thermus.flavus                  SDPNLQNIPVRTPLGQRIRRAFVAEEG-WVLVVLDYSQIELRVLAHLSGD  624
Thermus.oshimai                 SDPNLQNIPVRTPLGQRIRKAFIAEEG-HLLVALDYSQIELRVLAHLSGD  623
Thermus.filiformis              SDPNLQNIPVRTPLGQRIRKAFVAEEG-WLLAADYSQIELRVLAHLSGD   625
Thermotoga.maritima.MSB8        SDPNLQNLPTKSEEGKEIPKAIVPQDPNWWIVSADYSQIELRILAHLSGD  688
Thermotoga.neapolitana.DSM4359  SDPNLQNLPTKSEEGKEIPKAIVPQDPDWWIVSADYSQIELRILAHLSGD  688
                                *******:*.:: *:.**:*::.:      :: ********:*******

Thermus.Thermophilus.HB8        ENLIRVFQEGKDIHTQTASWMFGVPPEAVDPLMRRAAKTVNFGVLYGMSA  677
Thermus.caldophilus             ENLIRVFQEGKDIHTQTASWMFGVPPEAVDPLMRRAAKTVNFGVLYGMSA  677
Thermus.thermophilus.HB27       ENLIRVFQEGKDIHTQTASWMFGVPPEAVDPLMRRAAKTVNFGVLYGMSA  677
Thermus.aquaticus               ENLIRVFQEGPDIHTETASWMFGVPPEAVDPLMRRAAKTINFGVLYGMSA  675
Thermus.scotoductus             ENLIRVFQEGQDIHTQTASWMFGVPPEAVDSLMRRAAKTINFGVLYGMSA  676
Thermus.flavus                  ENLIRVFQEGRDIHTQTASWMFGVSPEGVDPLMRRAAKTINFGVLYGMSA  674
Thermus.oshimai                 ENLIRVFREGKDIHTETAAWMFGVPPEGVDGAMRRAAKTVNYGVLYGMSA  673
Thermus.filiformis              ENLKRVFREGKDIHTETAAWMFGLDPALVDPKMRRAAKTVNFGVLYGMSA  675
Thermotoga.maritima.MSB8        ENLLRAFEEGIDVHTLTASRIFNYKPEEVIEEMPRAGKMVNFSIIYGVTP  738
Thermotoga.neapolitana.DSM4359  ENLVKAFEEGIDVHTLTASRIYNYKPEEVNEEMRRVGKMVNFSIIYGVTP  738
                                ***  :.*.** *;** **: ::.:    *    ***..* :*:.::**:.

Thermus.Thermophilus.HB8        HRLSQELAIPYEEAVAFIERYFQSFPKVRAWIEKTLEEGRKPGYVETLFG  727
Thermus.caldophilus             HRLSQELAIPYEEAVAFIERYFQSFPKVRAWIEKTLEEGRKPGYVETLFG  727
Thermus.thermophilus.HB27       HRLSQELAIPYEEAVAFIERYFQSFPKVRAWIEKTLEEGRKRGYVETLFG  727
Thermus.aquaticus               HRLSQELAIPYEEAQAFIERYFQSFPKVPAWIEKTLEEGRRRGYVETLFG  725
Thermus.scotoductus             HRLSGELAIPYEEAVAFIERYFQSYPKVRAWIEKTLAEGRERGYVETLFG  726
Thermus.flavus                  HRLSGELSIPYEEAVAFIERYFQSYPKVRAWIEGTLEEGRPRGYVETLFG  724
Thermus.oshimai                 HRLSQELSIPYEEAAAFIERYFQSFPKVRAWIAKTLEEGPKKGYVETLFG  723
Thermus.filiformis              HRLSQELGIDYKEAEAFIERYFQSFPKVPAWIEPTLEEGRTRGYVETLFG  725
Thermotoga.maritima.MSB8        YGLSVRLGVPVKEAEKMIVNYFVLYPKVRDYIQRVVSEAKEKGYVRTLFG  788
Thermotoga.neapolitana.DSM4359  YGLSVRLGIPVKEAEKMIISYFTLYPKVRSYIQQVVAEAKEKGYVRTLFG  788
                                ; ** .*.:  :**  :*  **  :****  :*  .:  *.: :***.****
```

Figure 1 (cont.)

```
Thermus.Thermophilus.HB8         PPRYVPDLNAPVKSVREAAEPMAFNMPVQGTAADLMKLAMVKLFPPLR--  775
Thermus.caldophilus              RRRYVPDLNARVKSVPEAAERMAFNMPVQGTAADLMKLAMVKLFPPLR--  775
Thermus.thermophilus.HB27        PPRYVPDLNARVKSVREAAEPMAFNMPVQGTAADLMKLAMVKLFPPLR--  775
Thermus.aquaticus                RRRYVPDLEARVKSVPEAAEPMAFNRPVQGTAADLMKLAMVKLFPPLE--  773
Thermus.scotoductus              PPRYVPDLASPVKSIREAAERMAFNMPVQGTAADLMKLAMVKLFPPLQ--  774
Thermus.flavus                   RRRYVPDLNARVKSVPEAAEPMAFNRPVQGTAADLMKLAMVPLFPPLQ--  772
Thermus.oshimai                  PPPYVPDLNARVKSVREAAEPMAFNMPVQGTAADLMKLAMVKLFPPLR--  771
Thermus.filiformis               RRRYVPDLASRVRSVPEAAEPMAFNMPVQGTAADLMKIAMVELFPRLK--  773
Thermotoga.maritima.MSB8         RKPDIPQLMAPDRPTQAEGERIAINTPIQGTAADIIKLAMIEIDPELKER  838
Thermotoga.neapolitana.DSM4359   RKRDIPQLMARDKNTDSEGERIAINTPIQGTAADIIKLAMIDIDEELRKR  838
                                 *;*  :*;*  ;* :,   :   .**;*;* *;:******;;*;**;   .*.

Thermus.Thermophilus.HB8         EMGARMLLQVHDELLLEAPQARAEEVAALAKEAMEKAYPLAVPLEVEVGM  825
Thermus.caldophilus              EMGARMLLQVHDELLLEAPQAGAEEVAALAPEAMEKAYPLAVPLEVEVGM  825
Thermus.thermophilus.HB27        EMGARMLLQVHDELLLEAPQARAEEVAALAKEAMEKAYPLAVPLEVEVGI  825
Thermus.aquaticus                EMGARMLLQVHDELVLEAPHERAEAVARLAPEVMEGVYPLAVPLEVEVGI  823
Thermus.scotoductus              ELGARMLLQVHDELVLEAPKEQAEEVAQEAKRTHEEVWPLKVPLEVEVGI  824
Thermus.flavus                   ELGARMLLQVHDELVLEAPEDRAERVAALAPEVMEGVWPLQVPLEVEVGL  822
Thermus.oshimai                  PLGVRILLQVHDELVLEAPKARAEEAAQLAKETHEGVYPLSVPLEVEVGM  821
Thermus.filiformis               PLGARLLLQVHDELVLEVPEDRAEEAKALVEEVMENTYPLDVPLEVEVGV  823
Thermotoga.maritima.MSB8         KMPSKMIIQVHDELVFEVPNEEKDALVELVKDRMTNVVKLSVPLEVDVTI  888
Thermotoga.neapolitana.DSM4359   NMKSRMIIQVHDELVFEVPDEEKEELVDLVEMRMINVVKLSVPLEVDISI  888
                                  :  :::*******;;*.*.     ;    .*    *    * *****;; ;

Thermus.Thermophilus.HB8         GEDWLSAKG-  834    (SEQ ID NO:1)
Thermus.caldophilus              GEDWLSAKG-  834    (SEQ ID NO:2)
Thermus.thermophilus.HB27        GEDWLSAKG-  834    (SEQ ID NO:3)
Thermus.aquaticus                GEDWLSAKE-  832    (SEQ ID NO:4)
Thermus.scotoductus              GEDWLSAKA-  833    (SEQ ID NO:5)
Thermus.flavus                   GEDWLSAEE-  831    (SEQ ID NO:6)
Thermus.oshimai                  GEDWLSAKA-  830    (SEQ ID NO:7)
Thermus.filiformis               GRDWLEAKGD  833    (SEQ ID NO:8)
Thermotoga.maritima.MSB8         GKTWS-----  893    (SEQ ID NO:9)
Thermotoga.neapolitana.DSM4359   GKSWS-----  893    (SEQ ID NO:10)
                                 *. *
```

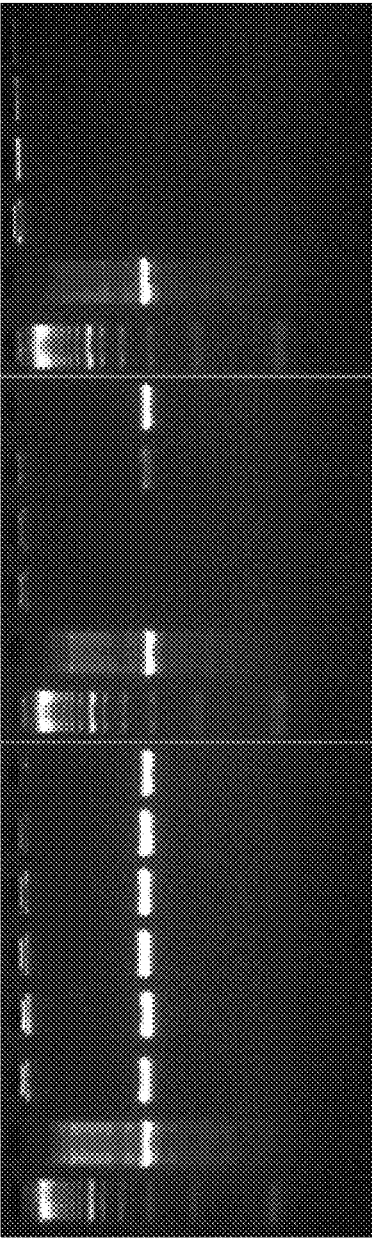
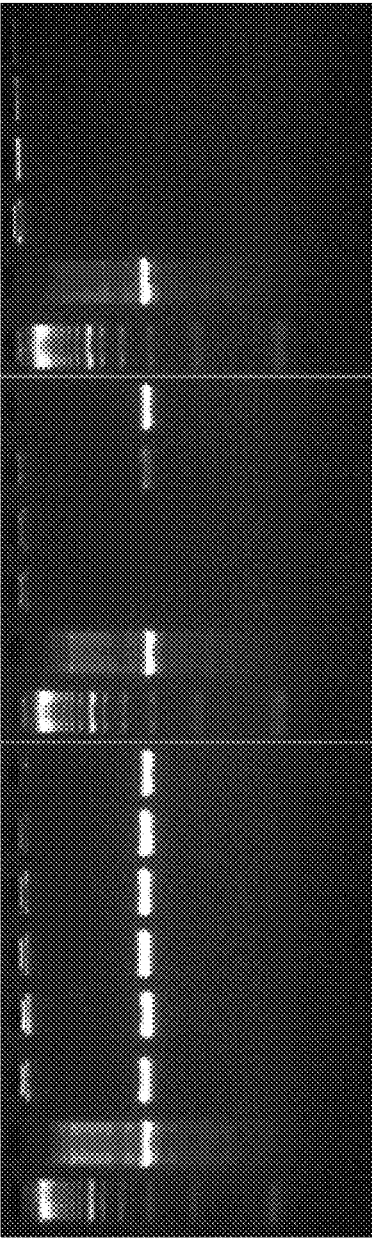
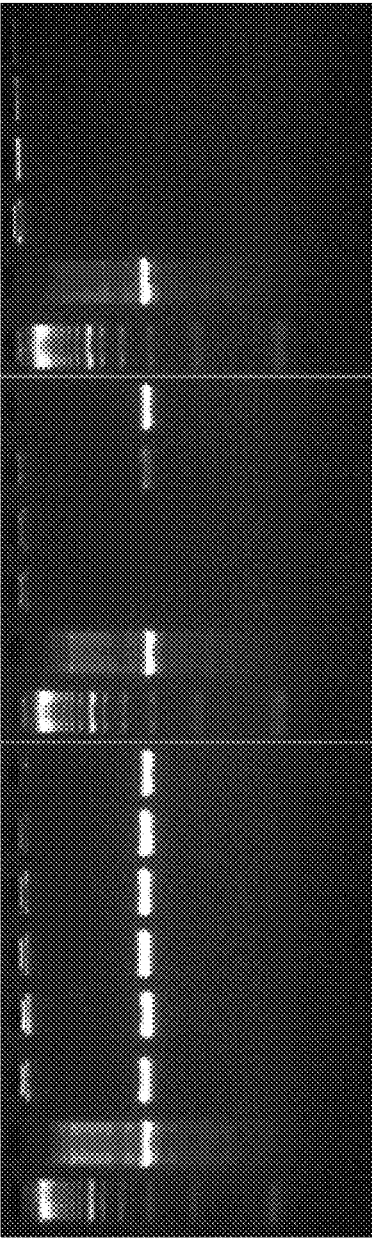
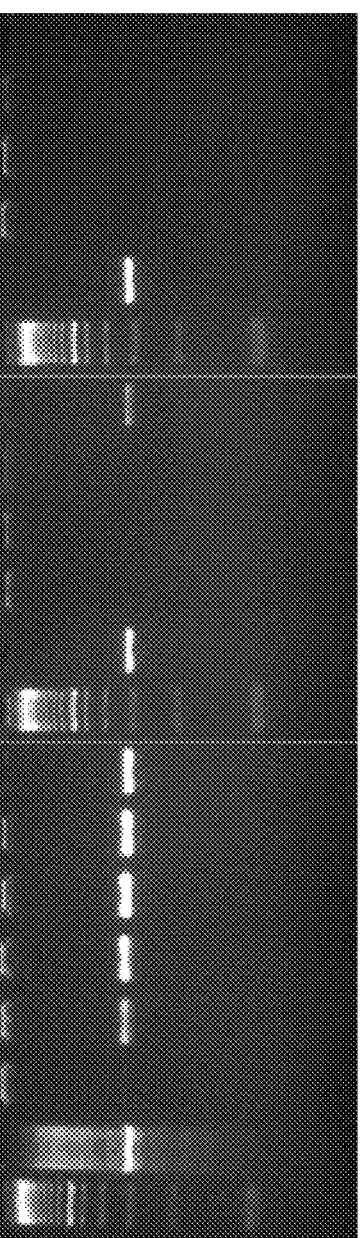
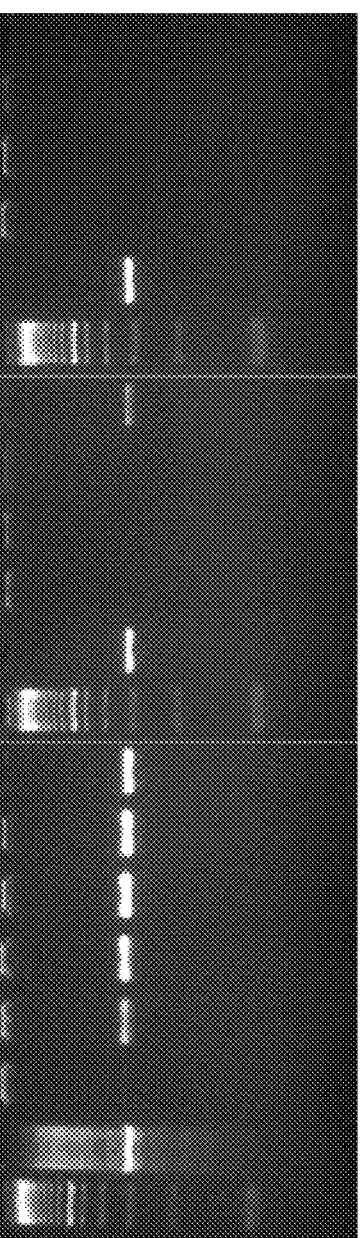
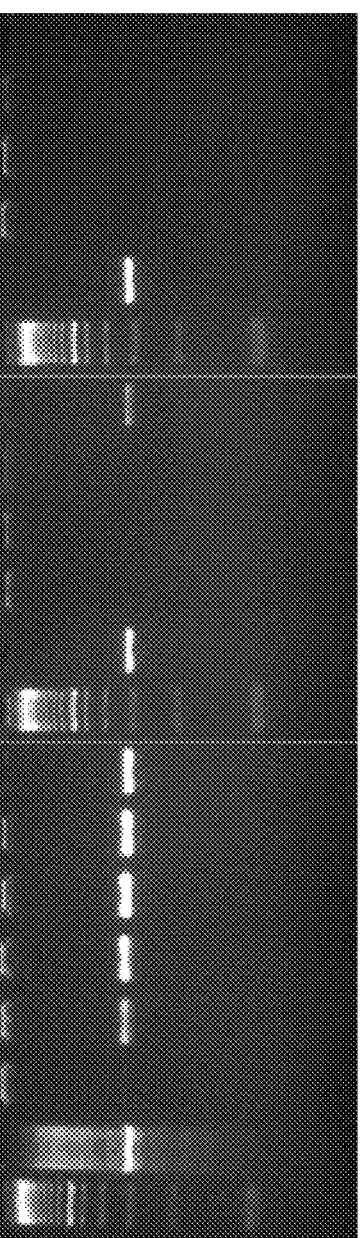

SEQUENCE LISTING

```
<160> NUMBER OF SEQ ID NOS: 12

<210> SEQ ID NO 1
<211> LENGTH: 834
<212> TYPE: PRT
<213> ORGANISM: Thermus thermophilus

<400> SEQUENCE: 1

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220
```

```
Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
            245                 250                 255

Glu Val Asp Leu Ala Gln Gly Arg Glu Pro Asp Arg Glu Gly Leu Arg
        260                 265                 270

Ala Phe Leu Glu Arg Leu Glu Phe Gly Ser Leu Leu His Glu Phe Gly
    275                 280                 285

Leu Leu Glu Ala Pro Ala Pro Leu Glu Glu Ala Pro Trp Pro Pro Pro
290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
        355                 360                 365

Leu Val Pro Gly Asp Asp Pro Met Leu Leu Ala Tyr Leu Leu Asp Pro
    370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

Asn Leu Leu Lys Arg Leu Glu Gly Glu Lys Leu Leu Trp Leu Tyr
            420                 425                 430

His Glu Val Glu Lys Pro Leu Ser Arg Val Leu Ala His Met Glu Ala
        435                 440                 445

Thr Gly Val Arg Arg Asp Val Ala Tyr Leu Gln Ala Leu Ser Leu Glu
    450                 455                 460

Leu Ala Glu Glu Ile Arg Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
        515                 520                 525

Pro Ile Val Glu Lys Ile Leu Gln His Arg Glu Leu Thr Lys Leu Lys
    530                 535                 540

Asn Thr Tyr Val Asp Pro Leu Pro Ser Leu Val His Pro Arg Thr Gly
545                 550                 555                 560

Arg Leu His Thr Arg Phe Asn Gln Thr Ala Thr Ala Thr Gly Arg Leu
                565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
        595                 600                 605

Val Ala Leu Asp Tyr Ser Gln Ile Glu Leu Arg Val Leu Ala His Leu
    610                 615                 620

Ser Gly Asp Glu Asn Leu Ile Arg Val Phe Gln Glu Gly Lys Asp Ile
625                 630                 635                 640
```

His Thr Gln Thr Ala Ser Trp Met Phe Gly Val Pro Glu Ala Val
                    645                 650                 655

Asp Pro Leu Met Arg Arg Ala Ala Lys Thr Val Asn Phe Gly Val Leu
        660                 665                 670

Tyr Gly Met Ser Ala His Arg Leu Ser Gln Glu Leu Ala Ile Pro Tyr
            675                 680                 685

Glu Glu Ala Val Ala Phe Ile Glu Arg Tyr Phe Gln Ser Phe Pro Lys
        690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Arg Tyr Val Pro Asp Leu Asn
                725                 730                 735

Ala Arg Val Lys Ser Val Arg Glu Ala Ala Glu Arg Met Ala Phe Asn
            740                 745                 750

Met Pro Val Gln Gly Thr Ala Ala Asp Leu Met Lys Leu Ala Met Val
        755                 760                 765

Lys Leu Phe Pro Arg Leu Arg Glu Met Gly Ala Arg Met Leu Leu Gln
    770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
                805                 810                 815

Val Pro Leu Glu Val Glu Val Gly Met Gly Glu Asp Trp Leu Ser Ala
            820                 825                 830

Lys Gly

<210> SEQ ID NO 2
<211> LENGTH: 834
<212> TYPE: PRT
<213> ORGANISM: Thermus aquaticus

<400> SEQUENCE: 2

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Tyr Lys Ala Val Phe
        50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Asn Pro Glu Lys Glu Gly Tyr Glu Val Arg Ile Leu Thr Ala Asp Arg
    130                 135                 140

Asp Leu Asp Gln Leu Val Ser Asp Arg Val Ala Val Leu His Pro Glu
145                 150                 155                 160

Gly His Leu Ile Thr Pro Glu Trp Leu Trp Gln Lys Tyr Gly Leu Lys
                165                 170                 175

```
Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
            195                 200                 205

Leu Lys Glu Trp Gly Ser Leu Glu Asn Leu Leu Lys Asn Leu Asp Arg
            210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
            245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
            275                 280                 285

Leu Leu Glu Ala Pro Ala Pro Leu Glu Glu Ala Pro Trp Pro Pro Pro
            290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
            325                 330                 335

Ala Ala Asp Pro Leu Ala Gly Leu Lys Asp Leu Lys Glu Val Arg Gly
            340                 345                 350

Leu Leu Ala Lys Asp Leu Ala Val Leu Ala Ser Arg Glu Gly Leu Asp
            355                 360                 365

Leu Val Pro Gly Asp Asp Pro Met Leu Leu Ala Tyr Leu Leu Asp Pro
            370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
            405                 410                 415

Asn Leu Leu Lys Arg Leu Gln Gly Glu Glu Lys Leu Leu Trp Leu Tyr
            420                 425                 430

His Glu Val Glu Lys Pro Leu Ser Arg Val Leu Ala His Met Glu Ala
            435                 440                 445

Thr Gly Val Arg Leu Asp Val Ala Tyr Leu Gln Ala Leu Ser Leu Glu
            450                 455                 460

Leu Ala Glu Glu Ile Arg Arg Leu Glu Glu Glu Val Phe Arg Leu Ala
465                 470                 475                 480

Gly His Pro Phe Asn Leu Asn Ser Arg Asp Gln Leu Glu Arg Val Leu
            485                 490                 495

Phe Asp Glu Leu Arg Leu Pro Ala Leu Gly Lys Thr Gln Lys Thr Gly
            500                 505                 510

Lys Arg Ser Thr Ser Ala Ala Val Leu Glu Ala Leu Arg Glu Ala His
            515                 520                 525

Pro Ile Val Glu Lys Ile Leu Gln His Arg Glu Leu Thr Lys Leu Lys
            530                 535                 540

Asn Thr Tyr Val Asp Pro Leu Pro Ser Leu Val His Pro Asn Thr Gly
545                 550                 555                 560

Arg Leu His Thr Arg Phe Asn Gln Thr Ala Thr Ala Thr Gly Arg Leu
            565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
```

```
                    595                 600                 605
Val Ala Leu Asp Tyr Ser Gln Ile Glu Leu Arg Val Leu Ala His Leu
    610                 615                 620

Ser Gly Asp Glu Asn Leu Ile Arg Val Phe Gln Gly Lys Asp Ile
625                 630                 635                 640

His Thr Gln Thr Ala Ser Trp Met Phe Gly Val Pro Pro Glu Ala Val
                    645                 650                 655

Asp Pro Leu Met Arg Arg Ala Ala Lys Thr Val Asn Phe Gly Val Leu
            660                 665                 670

Tyr Gly Met Ser Ala His Arg Leu Ser Gln Glu Leu Ala Ile Pro Tyr
        675                 680                 685

Glu Glu Ala Val Ala Phe Ile Glu Arg Tyr Phe Gln Ser Phe Pro Lys
    690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Arg Tyr Val Pro Asp Leu Asn
                    725                 730                 735

Ala Arg Val Lys Ser Val Arg Glu Ala Ala Glu Arg Met Ala Phe Asn
            740                 745                 750

Met Pro Val Gln Gly Thr Ala Ala Asp Leu Met Lys Leu Ala Met Val
        755                 760                 765

Lys Leu Phe Pro Arg Leu Arg Glu Met Gly Ala Arg Met Leu Leu Gln
    770                 775                 780

Val His Asp Glu Leu Leu Leu Glu Ala Pro Gln Ala Gly Ala Glu Glu
785                 790                 795                 800

Val Ala Ala Leu Ala Lys Glu Ala Met Glu Lys Ala Tyr Pro Leu Ala
                    805                 810                 815

Val Pro Leu Glu Val Glu Val Gly Met Gly Glu Asp Trp Leu Ser Ala
            820                 825                 830

Lys Gly

<210> SEQ ID NO 3
<211> LENGTH: 834
<212> TYPE: PRT
<213> ORGANISM: Thermus thermophilus

<400> SEQUENCE: 3

Met Glu Ala Met Leu Pro Leu Phe Glu Ser Lys Gly Arg Val Leu Leu
1               5                   10                  15

Val Asp Gly His His Leu Ala Tyr Arg Thr Phe Phe Ala Leu Lys Gly
                    20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Tyr Lys Ser Val Phe
        50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                    85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125

Lys Ala Glu Lys Glu Gly Tyr Glu Val Arg Ile Leu Thr Ala Asp Arg
```

```
            130                 135                 140
Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
                180                 185                 190

Asn Leu Pro Gly Val Lys Gly Ile Gly Glu Lys Thr Ala Leu Lys Leu
                195                 200                 205

Leu Lys Glu Trp Gly Ser Leu Glu Ser Leu Leu Lys Asn Leu Asp Arg
            210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Ala Asp Leu Pro Leu
                245                 250                 255

Glu Val Asp Leu Ala Gln Gly Arg Glu Pro Asp Arg Glu Gly Leu Arg
                260                 265                 270

Ala Phe Leu Glu Arg Leu Glu Phe Gly Ser Leu Leu His Glu Phe Gly
            275                 280                 285

Leu Leu Glu Ala Pro Thr Pro Leu Glu Glu Ala Pro Trp Pro Pro
290                 295                 300

Glu Gly Ala Phe Val Gly Phe Val Leu Ser Arg Pro Glu Pro Met Trp
305                 310                 315                 320

Ala Glu Leu Lys Ala Leu Ala Ala Cys Arg Asp Gly Arg Val His Arg
                325                 330                 335

Ala Glu Asp Pro Leu Ala Gly Leu Gly Asp Leu Glu Glu Val Arg Gly
                340                 345                 350

Leu Leu Ala Lys Asp Leu Ala Val Leu Ala Leu Arg Glu Gly Leu Asp
                355                 360                 365

Leu Ala Pro Gly Asp Asp Pro Met Leu Leu Ala Tyr Leu Leu Asp Pro
            370                 375                 380

Ser Asn Thr Thr Pro Glu Gly Val Ala Arg Arg Tyr Gly Gly Glu Trp
385                 390                 395                 400

Thr Glu Asp Ala Ala His Arg Ala Leu Leu Ser Glu Arg Leu His Arg
                405                 410                 415

Asn Leu Leu Lys Arg Leu Glu Gly Glu Glu Lys Leu Leu Trp Leu Tyr
                420                 425                 430

His Glu Val Glu Lys Pro Leu Ser Arg Val Leu Ala His Met Glu Ala
            435                 440                 445

Thr Gly Val Arg Leu Asp Val Ala Tyr Leu Gln Ala Leu Ser Leu Glu
            450                 455                 460

Leu Ala Glu Glu Ile Arg Leu Glu Glu Val Phe Arg Leu Ala
465                 470                 475                 480

Gly His Pro Phe Asn Leu Asn Ser Arg Asp Gln Leu Glu Arg Val Leu
                485                 490                 495

Phe Asp Glu Leu Arg Leu Pro Ala Leu Gly Lys Thr Gln Lys Thr Gly
                500                 505                 510

Lys Arg Ser Thr Ser Ala Ala Val Leu Glu Ala Leu Arg Glu Ala His
            515                 520                 525

Pro Ile Val Glu Lys Ile Leu Gln His Arg Glu Leu Thr Lys Leu Lys
            530                 535                 540

Asn Thr Tyr Val Asp Pro Leu Pro Ser Leu Val His Pro Arg Thr Gly
545                 550                 555                 560
```

```
Arg Leu His Thr Arg Phe Asn Gln Thr Ala Thr Ala Thr Gly Arg Leu
            565                 570                 575

Ser Ser Ser Asp Pro Asn Leu Gln Asn Ile Pro Val Arg Thr Pro Leu
            580                 585                 590

Gly Gln Arg Ile Arg Arg Ala Phe Val Ala Glu Ala Gly Trp Ala Leu
            595                 600                 605

Val Ala Leu Asp Tyr Ser Gln Ile Glu Leu Arg Val Leu Ala His Leu
            610                 615                 620

Ser Gly Asp Glu Asn Leu Ile Arg Val Phe Gln Gly Lys Asp Ile
625                 630                 635                 640

His Thr Gln Thr Ala Ser Trp Met Phe Gly Val Pro Pro Glu Ala Val
            645                 650                 655

Asp Pro Leu Met Arg Arg Ala Ala Lys Thr Val Asn Phe Gly Val Leu
            660                 665                 670

Tyr Gly Met Ser Ala His Arg Leu Ser Gln Glu Leu Ala Ile Pro Tyr
            675                 680                 685

Glu Glu Ala Val Ala Phe Ile Glu Arg Tyr Phe Gln Ser Phe Pro Lys
            690                 695                 700

Val Arg Ala Trp Ile Glu Lys Thr Leu Glu Glu Gly Arg Lys Arg Gly
705                 710                 715                 720

Tyr Val Glu Thr Leu Phe Gly Arg Arg Arg Tyr Val Pro Asp Leu Asn
            725                 730                 735

Ala Arg Val Lys Ser Val Arg Glu Ala Ala Glu Arg Met Ala Phe Asn
            740                 745                 750

Met Pro Val Gln Gly Thr Ala Ala Asp Leu Met Lys Leu Ala Met Val
            755                 760                 765

Lys Leu Phe Pro Arg Leu Arg Glu Met Gly Ala Arg Met Leu Leu Gln
            770                 775                 780

Val His Asp Glu Leu Leu Leu Glu Ala Pro Gln Ala Arg Ala Glu Glu
785                 790                 795                 800

Val Ala Ala Leu Ala Lys Glu Ala Met Glu Lys Ala Tyr Pro Leu Ala
            805                 810                 815

Val Pro Leu Glu Val Glu Val Gly Ile Gly Glu Asp Trp Leu Ser Ala
            820                 825                 830

Lys Gly

<210> SEQ ID NO 4
<211> LENGTH: 832
<212> TYPE: PRT
<213> ORGANISM: Thermus aquaticus

<400> SEQUENCE: 4

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
            20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Gly Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
            85                  90                  95
```

```
Ala Leu Ile Lys Glu Leu Val Asp Leu Gly Leu Ala Arg Leu Glu
                100             105             110

Val Pro Gly Tyr Glu Ala Asp Val Leu Ala Ser Leu Ala Lys Lys
            115             120             125

Ala Glu Lys Glu Gly Tyr Glu Val Arg Ile Leu Thr Ala Asp Lys Asp
        130             135             140

Leu Tyr Gln Leu Leu Ser Asp Arg Ile His Val Leu His Pro Glu Gly
145             150             155             160

Tyr Leu Ile Thr Pro Ala Trp Leu Trp Glu Lys Tyr Gly Leu Arg Pro
                165             170             175

Asp Gln Trp Ala Asp Tyr Arg Ala Leu Thr Gly Asp Glu Ser Asp Asn
            180             185             190

Leu Pro Gly Val Lys Gly Ile Gly Glu Lys Thr Ala Arg Lys Leu Leu
        195             200             205

Glu Glu Trp Gly Ser Leu Glu Ala Leu Leu Lys Asn Leu Asp Arg Leu
210             215             220

Lys Pro Ala Ile Arg Glu Lys Ile Leu Ala His Met Asp Asp Leu Lys
225             230             235             240

Leu Ser Trp Asp Leu Ala Lys Val Arg Thr Asp Leu Pro Leu Glu Val
                245             250             255

Asp Phe Ala Lys Arg Arg Glu Pro Asp Arg Glu Arg Leu Arg Ala Phe
            260             265             270

Leu Glu Arg Leu Glu Phe Gly Ser Leu Leu His Glu Phe Gly Leu Leu
        275             280             285

Glu Ser Pro Lys Ala Leu Glu Glu Ala Pro Trp Pro Pro Glu Gly
290             295             300

Ala Phe Val Gly Phe Val Leu Ser Arg Lys Glu Pro Met Trp Ala Asp
305             310             315             320

Leu Leu Ala Leu Ala Ala Ala Arg Gly Gly Arg Val His Arg Ala Pro
                325             330             335

Glu Pro Tyr Lys Ala Leu Arg Asp Leu Lys Glu Ala Arg Gly Leu Leu
            340             345             350

Ala Lys Asp Leu Ser Val Leu Ala Leu Arg Glu Gly Leu Gly Leu Pro
        355             360             365

Pro Gly Asp Asp Pro Met Leu Leu Ala Tyr Leu Leu Asp Pro Ser Asn
370             375             380

Thr Thr Pro Glu Gly Val Ala Arg Arg Tyr Gly Gly Glu Trp Thr Glu
385             390             395             400

Glu Ala Gly Glu Arg Ala Ala Leu Ser Glu Arg Leu Phe Ala Asn Leu
                405             410             415

Trp Gly Arg Leu Glu Gly Glu Glu Arg Leu Leu Trp Leu Tyr Arg Glu
            420             425             430

Val Glu Arg Pro Leu Ser Ala Val Leu Ala His Met Glu Ala Thr Gly
        435             440             445

Val Arg Leu Asp Val Ala Tyr Leu Arg Ala Leu Ser Leu Glu Val Ala
450             455             460

Glu Glu Ile Ala Arg Leu Glu Ala Glu Val Phe Arg Leu Ala Gly His
465             470             475             480

Pro Phe Asn Leu Asn Ser Arg Asp Gln Leu Glu Arg Val Leu Phe Asp
                485             490             495

Glu Leu Gly Leu Pro Ala Ile Gly Lys Thr Glu Lys Thr Gly Lys Arg
            500             505             510
```

Ser Thr Ser Ala Ala Val Leu Glu Ala Leu Arg Glu Ala His Pro Ile
            515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
            580                 585                 590

Arg Ile Arg Arg Ala Phe Ile Ala Glu Glu Gly Trp Leu Leu Val Ala
            595                 600                 605

Leu Asp Tyr Ser Gln Ile Glu Leu Arg Val Leu Ala His Leu Ser Gly
        610                 615                 620

Asp Glu Asn Leu Ile Arg Val Phe Gln Glu Gly Arg Asp Ile His Thr
625                 630                 635                 640

Glu Thr Ala Ser Trp Met Phe Gly Val Pro Arg Glu Ala Val Asp Pro
                645                 650                 655

Leu Met Arg Arg Ala Ala Lys Thr Ile Asn Phe Gly Val Leu Tyr Gly
            660                 665                 670

Met Ser Ala His Arg Leu Ser Gln Glu Leu Ala Ile Pro Tyr Glu Glu
            675                 680                 685

Ala Gln Ala Phe Ile Glu Arg Tyr Phe Gln Ser Phe Pro Lys Val Arg
            690                 695                 700

Ala Trp Ile Glu Lys Thr Leu Glu Glu Gly Arg Arg Arg Gly Tyr Val
705                 710                 715                 720

Glu Thr Leu Phe Gly Arg Arg Arg Tyr Val Pro Asp Leu Glu Ala Arg
                725                 730                 735

Val Lys Ser Val Arg Glu Ala Ala Glu Arg Met Ala Phe Asn Met Pro
            740                 745                 750

Val Gln Gly Thr Ala Ala Asp Leu Met Lys Leu Ala Met Val Lys Leu
            755                 760                 765

Phe Pro Arg Leu Glu Glu Met Gly Ala Arg Met Leu Leu Gln Val His
    770                 775                 780

Asp Glu Leu Val Leu Glu Ala Pro Lys Glu Arg Ala Glu Ala Val Ala
785                 790                 795                 800

Arg Leu Ala Lys Glu Val Met Glu Gly Val Tyr Pro Leu Ala Val Pro
                805                 810                 815

Leu Glu Val Glu Val Gly Ile Gly Glu Asp Trp Leu Ser Ala Lys Glu
            820                 825                 830

<210> SEQ ID NO 5
<211> LENGTH: 833
<212> TYPE: PRT
<213> ORGANISM: Thermus scotoductus

<400> SEQUENCE: 5

Met Arg Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Arg Glu Asp Gly Asp Val Val Ile Val
    50                  55                  60

-continued

```
Val Phe Asp Ala Lys Ala Pro Ser Phe Arg His Gln Thr Tyr Glu Ala
 65                  70                  75                  80

Tyr Lys Ala Gly Arg Ala Pro Thr Pro Glu Asp Phe Pro Arg Gln Leu
                 85                  90                  95

Ala Leu Ile Lys Glu Met Val Asp Leu Leu Gly Leu Glu Arg Leu Glu
            100                 105                 110

Val Pro Gly Phe Glu Ala Asp Asp Val Leu Ala Thr Leu Ala Lys Lys
        115                 120                 125

Ala Glu Lys Glu Gly Tyr Glu Val Arg Ile Leu Thr Ala Asp Arg Asp
130                 135                 140

Leu Tyr Gln Leu Leu Ser Glu Arg Ile Ser Ile Leu His Pro Glu Gly
145                 150                 155                 160

Tyr Leu Ile Thr Pro Glu Trp Leu Trp Glu Lys Tyr Gly Leu Lys Pro
                165                 170                 175

Ser Gln Trp Val Asp Tyr Arg Ala Leu Ala Gly Asp Pro Ser Asp Asn
            180                 185                 190

Ile Pro Gly Val Lys Gly Ile Gly Glu Lys Thr Ala Ala Lys Leu Ile
        195                 200                 205

Arg Glu Trp Gly Ser Leu Glu Asn Leu Leu Lys His Leu Glu Gln Val
210                 215                 220

Lys Pro Ala Ser Val Arg Glu Lys Ile Leu Ser His Met Glu Asp Leu
225                 230                 235                 240

Lys Leu Ser Leu Glu Leu Ser Arg Val Arg Thr Asp Leu Pro Leu Gln
                245                 250                 255

Val Asp Phe Ala Arg Arg Arg Glu Pro Asp Arg Glu Gly Leu Lys Ala
            260                 265                 270

Phe Leu Glu Arg Leu Glu Phe Gly Ser Leu Leu His Glu Phe Gly Leu
        275                 280                 285

Leu Glu Ser Pro Val Ala Ala Glu Gly Ala Pro Trp Pro Pro Pro Glu
290                 295                 300

Gly Ala Phe Val Gly Tyr Val Leu Ser Arg Pro Glu Pro Met Trp Ala
305                 310                 315                 320

Glu Leu Asn Ala Leu Ala Ala Ala Trp Glu Gly Arg Val Tyr Arg Ala
                325                 330                 335

Glu Asp Pro Leu Glu Ala Leu Arg Gly Leu Gly Glu Val Arg Gly Leu
            340                 345                 350

Leu Ala Lys Asp Leu Ala Val Leu Ala Leu Arg Glu Gly Ile Ala Leu
        355                 360                 365

Ala Pro Gly Asp Asp Pro Met Leu Leu Ala Tyr Leu Leu Asp Pro Ser
370                 375                 380

Asn Thr Ala Pro Glu Gly Val Ala Arg Arg Tyr Gly Gly Glu Trp Thr
385                 390                 395                 400

Glu Glu Ala Gly Glu Arg Ala Leu Leu Ser Glu Arg Leu Tyr Ala Ala
                405                 410                 415

Leu Leu Glu Arg Leu Lys Gly Glu Glu Arg Leu Leu Trp Leu Tyr Glu
            420                 425                 430

Glu Val Glu Lys Pro Leu Ser Arg Val Leu Ala His Met Glu Ala Thr
        435                 440                 445

Gly Val Arg Leu Asp Val Ala Tyr Leu Lys Ala Leu Ser Leu Glu Val
450                 455                 460

Glu Ala Glu Leu Arg Arg Leu Glu Glu Glu Val His Arg Leu Ala Gly
465                 470                 475                 480
```

-continued

His Pro Phe Asn Leu Asn Ser Arg Asp Gln Leu Glu Arg Val Leu Phe
                485                 490                 495

Asp Glu Leu Gly Leu Pro Ala Ile Gly Lys Thr Glu Lys Thr Gly Lys
            500                 505                 510

Arg Ser Thr Ser Ala Ala Val Leu Glu Ala Leu Arg Glu Ala His Pro
            515                 520                 525

Ile Val Asp Arg Ile Leu Gln Tyr Arg Glu Leu Ser Lys Leu Lys Gly
            530                 535                 540

Thr Tyr Ile Asp Pro Leu Pro Ala Leu Val His Pro Lys Thr Asn Arg
545                 550                 555                 560

Leu His Thr Arg Phe Asn Gln Thr Ala Thr Ala Thr Gly Arg Leu Ser
                565                 570                 575

Ser Ser Asp Pro Asn Leu Gln Asn Ile Pro Val Arg Thr Pro Leu Gly
            580                 585                 590

Gln Arg Ile Arg Arg Ala Phe Val Ala Glu Glu Gly Trp Arg Leu Val
            595                 600                 605

Val Leu Asp Tyr Ser Gln Ile Glu Leu Arg Val Leu Ala His Leu Ser
            610                 615                 620

Gly Asp Glu Asn Leu Ile Arg Val Phe Gln Glu Gly Gln Asp Ile His
625                 630                 635                 640

Thr Gln Thr Ala Ser Trp Met Phe Gly Val Pro Pro Glu Ala Val Asp
                645                 650                 655

Ser Leu Met Arg Arg Ala Ala Lys Thr Ile Asn Phe Gly Val Leu Tyr
            660                 665                 670

Gly Met Ser Ala His Arg Leu Ser Gly Glu Leu Ala Ile Pro Tyr Glu
            675                 680                 685

Glu Ala Val Ala Phe Ile Glu Arg Tyr Phe Gln Ser Tyr Pro Lys Val
            690                 695                 700

Arg Ala Trp Ile Glu Lys Thr Leu Ala Glu Gly Arg Glu Arg Gly Tyr
705                 710                 715                 720

Val Glu Thr Leu Phe Gly Arg Arg Arg Tyr Val Pro Asp Leu Ala Ser
                725                 730                 735

Arg Val Lys Ser Ile Arg Glu Ala Ala Glu Arg Met Ala Phe Asn Met
            740                 745                 750

Pro Val Gln Gly Thr Ala Ala Asp Leu Met Lys Leu Ala Met Val Lys
            755                 760                 765

Leu Phe Pro Arg Leu Gln Glu Leu Gly Ala Arg Met Leu Leu Gln Val
            770                 775                 780

His Asp Glu Leu Val Leu Glu Ala Pro Lys Glu Gln Ala Glu Val
785                 790                 795                 800

Ala Gln Glu Ala Lys Arg Thr Met Glu Glu Val Trp Pro Leu Lys Val
                805                 810                 815

Pro Leu Glu Val Glu Val Gly Ile Gly Glu Asp Trp Leu Ser Ala Lys
            820                 825                 830

Ala

<210> SEQ ID NO 6
<211> LENGTH: 831
<212> TYPE: PRT
<213> ORGANISM: Thermus aquaticus

<400> SEQUENCE: 6

Met Ala Met Leu Pro Leu Phe Glu Pro Lys Gly Arg Val Leu Leu Val
1               5                   10                  15

-continued

```
Asp Gly His His Leu Ala Tyr Arg Thr Phe Ala Leu Lys Gly Leu
             20                  25                  30
Thr Thr Ser Arg Gly Glu Pro Val Gln Ala Val Tyr Gly Phe Ala Lys
         35                  40                  45
Ser Leu Leu Lys Ala Leu Lys Glu Asp Gly Asp Val Val Val Val
 50                  55                  60
Phe Asp Ala Lys Ala Pro Ser Phe Arg His Glu Ala Tyr Glu Ala Tyr
 65              70                  75                  80
Lys Ala Gly Arg Ala Pro Thr Pro Glu Asp Phe Pro Arg Gln Leu Ala
             85                  90                  95
Leu Ile Lys Glu Leu Val Asp Leu Leu Gly Leu Val Arg Leu Glu Val
            100                 105                 110
Pro Gly Phe Glu Ala Asp Asp Val Leu Ala Thr Leu Ala Lys Arg Ala
            115                 120                 125
Glu Lys Glu Gly Tyr Glu Val Arg Ile Leu Thr Ala Asp Arg Asp Leu
            130                 135                 140
Tyr Gln Leu Leu Ser Glu Arg Ile Ala Ile Leu His Pro Glu Gly Tyr
145                 150                 155                 160
Leu Ile Thr Pro Ala Trp Leu Tyr Glu Lys Tyr Gly Leu Arg Pro Glu
                165                 170                 175
Gln Trp Val Asp Tyr Arg Ala Leu Ala Gly Asp Pro Ser Asp Asn Ile
            180                 185                 190
Pro Gly Val Lys Gly Ile Gly Glu Lys Thr Ala Gln Arg Leu Ile Arg
            195                 200                 205
Glu Trp Gly Ser Leu Glu Asn Leu Phe Gln His Leu Asp Gln Val Lys
210                 215                 220
Pro Ser Leu Arg Glu Lys Leu Gln Ala Gly Met Glu Ala Leu Ala Leu
225                 230                 235                 240
Ser Arg Lys Leu Ser Gln Val His Thr Asp Leu Pro Leu Glu Val Asp
                245                 250                 255
Phe Gly Arg Arg Thr Pro Asn Leu Glu Gly Leu Arg Ala Phe Leu
            260                 265                 270
Glu Arg Leu Glu Phe Gly Ser Leu Leu His Glu Phe Gly Leu Leu Glu
            275                 280                 285
Gly Pro Lys Ala Ala Glu Glu Ala Pro Trp Pro Pro Glu Gly Ala
290                 295                 300
Phe Leu Gly Phe Ser Phe Ser Arg Pro Glu Pro Met Trp Ala Glu Leu
305                 310                 315                 320
Leu Ala Leu Ala Gly Ala Trp Glu Gly Arg Leu His Arg Ala Gln Asp
                325                 330                 335
Pro Leu Arg Gly Leu Arg Asp Leu Lys Gly Val Arg Gly Ile Leu Ala
            340                 345                 350
Lys Asp Leu Ala Val Leu Ala Leu Arg Glu Gly Leu Asp Leu Phe Pro
            355                 360                 365
Glu Asp Asp Pro Met Leu Leu Ala Tyr Leu Leu Asp Pro Ser Asn Thr
            370                 375                 380
Thr Pro Glu Gly Val Ala Arg Arg Tyr Gly Gly Glu Trp Thr Glu Asp
385                 390                 395                 400
Ala Gly Glu Arg Ala Leu Leu Ala Glu Arg Leu Phe Gln Thr Leu Lys
                405                 410                 415
Glu Arg Leu Lys Gly Glu Glu Arg Leu Leu Trp Leu Tyr Glu Glu Val
            420                 425                 430
Glu Lys Pro Leu Ser Arg Val Leu Ala Arg Met Glu Ala Thr Gly Val
```

```
                    435                 440                 445
Arg Leu Asp Val Ala Tyr Leu Gln Ala Leu Ser Leu Glu Val Glu Ala
        450                 455                 460

Glu Val Arg Gln Leu Glu Glu Val Phe Arg Leu Ala Gly His Pro
465                 470                 475                 480

Phe Asn Leu Asn Ser Arg Asp Gln Leu Glu Arg Val Leu Phe Asp Glu
                    485                 490                 495

Leu Gly Leu Pro Ala Ile Gly Lys Thr Glu Lys Thr Gly Lys Arg Ser
            500                 505                 510

Thr Ser Ala Ala Val Leu Glu Ala Leu Arg Glu Ala His Pro Ile Val
        515                 520                 525

Asp Arg Ile Leu Gln Tyr Arg Glu Leu Thr Lys Leu Lys Asn Thr Tyr
    530                 535                 540

Ile Asp Pro Leu Pro Ala Leu Val His Pro Lys Thr Gly Arg Leu His
545                 550                 555                 560

Thr Arg Phe Asn Gln Thr Ala Thr Ala Thr Gly Arg Leu Ser Ser Ser
                    565                 570                 575

Asp Pro Asn Leu Gln Asn Ile Pro Val Arg Thr Pro Leu Gly Gln Arg
            580                 585                 590

Ile Arg Arg Ala Phe Val Ala Glu Glu Gly Trp Val Leu Val Val Leu
        595                 600                 605

Asp Tyr Ser Gln Ile Glu Leu Arg Val Leu Ala His Leu Ser Gly Asp
    610                 615                 620

Glu Asn Leu Ile Arg Val Phe Gln Gly Arg Asp Ile His Thr Gln
625                 630                 635                 640

Thr Ala Ser Trp Met Phe Gly Val Ser Pro Glu Gly Val Asp Pro Leu
                    645                 650                 655

Met Arg Ala Ala Lys Thr Ile Asn Phe Gly Val Leu Tyr Gly Met
            660                 665                 670

Ser Ala His Arg Leu Ser Gly Glu Leu Ser Ile Pro Tyr Glu Glu Ala
        675                 680                 685

Val Ala Phe Ile Glu Arg Tyr Phe Gln Ser Tyr Pro Lys Val Arg Ala
    690                 695                 700

Trp Ile Glu Gly Thr Leu Glu Glu Gly Arg Arg Arg Gly Tyr Val Glu
705                 710                 715                 720

Thr Leu Phe Gly Arg Arg Arg Tyr Val Pro Asp Leu Asn Ala Arg Val
                    725                 730                 735

Lys Ser Val Arg Glu Ala Ala Glu Arg Met Ala Phe Asn Met Pro Val
            740                 745                 750

Gln Gly Thr Ala Ala Asp Leu Met Lys Leu Ala Met Val Arg Leu Phe
        755                 760                 765

Pro Arg Leu Gln Glu Leu Gly Ala Arg Met Leu Leu Gln Val His Asp
    770                 775                 780

Glu Leu Val Leu Glu Ala Pro Lys Asp Arg Ala Glu Arg Val Ala Ala
785                 790                 795                 800

Leu Ala Lys Glu Val Met Glu Gly Val Trp Pro Leu Gln Val Pro Leu
                    805                 810                 815

Glu Val Glu Val Gly Leu Gly Glu Asp Trp Leu Ser Ala Lys Glu
            820                 825                 830

<210> SEQ ID NO 7
<211> LENGTH: 830
<212> TYPE: PRT
<213> ORGANISM: Thermus oshimai
```

<400> SEQUENCE: 7

```
Met Leu Pro Leu Phe Glu Pro Lys Gly Arg Val Leu Val Asp Gly
1               5                   10                  15

His His Leu Ala Tyr Arg Thr Phe Phe Ala Leu Lys Gly Leu Thr Thr
            20                  25                  30

Ser Arg Gly Glu Pro Val Gln Ala Val Tyr Asp Phe Ala Lys Ser Leu
        35                  40                  45

Leu Lys Ala Leu Lys Glu Asp Gly Glu Val Ala Ile Val Val Phe Asp
    50                  55                  60

Ala Lys Ala Pro Ser Phe Arg His Glu Ala Tyr Glu Ala Tyr Lys Ala
65                  70                  75                  80

Gly Arg Ala Pro Thr Pro Glu Asp Phe Pro Arg Gln Leu Ala Leu Ile
                85                  90                  95

Lys Glu Leu Val Asp Leu Leu Gly Leu Val Arg Leu Glu Val Pro Gly
            100                 105                 110

Phe Glu Ala Asp Asp Val Leu Ala Thr Leu Ala Lys Lys Ala Glu Arg
        115                 120                 125

Glu Gly Tyr Glu Val Arg Ile Leu Ser Ala Asp Arg Asp Leu Tyr Gln
    130                 135                 140

Leu Leu Ser Asp Arg Ile His Leu His Pro Glu Gly Glu Val Leu
145                 150                 155                 160

Thr Pro Gly Trp Leu Gln Glu Arg Tyr Gly Leu Ser Pro Glu Arg Trp
                165                 170                 175

Val Glu Tyr Arg Ala Leu Val Gly Asp Pro Ser Asp Asn Leu Pro Gly
            180                 185                 190

Val Pro Gly Ile Gly Glu Lys Thr Ala Leu Lys Leu Leu Lys Glu Trp
        195                 200                 205

Gly Ser Leu Glu Ala Ile Leu Lys Asn Leu Asp Gln Val Lys Pro Glu
    210                 215                 220

Arg Val Arg Glu Ala Ile Arg Asn Asn Leu Asp Lys Leu Gln Met Ser
225                 230                 235                 240

Leu Glu Leu Ser Arg Leu Arg Thr Asp Leu Pro Leu Glu Val Asp Phe
                245                 250                 255

Ala Lys Arg Arg Glu Pro Asp Trp Glu Gly Leu Lys Ala Phe Leu Glu
            260                 265                 270

Arg Leu Glu Phe Gly Ser Leu Leu His Glu Phe Gly Leu Leu Glu Ala
        275                 280                 285

Pro Lys Glu Ala Glu Glu Ala Pro Trp Pro Pro Pro Gly Gly Ala Phe
    290                 295                 300

Leu Gly Phe Leu Leu Ser Arg Pro Glu Pro Met Trp Ala Glu Leu Leu
305                 310                 315                 320

Ala Leu Ala Gly Ala Lys Glu Gly Arg Val His Arg Ala Glu Asp Pro
                325                 330                 335

Val Gly Ala Leu Lys Asp Leu Lys Glu Ile Arg Gly Leu Leu Ala Lys
            340                 345                 350

Asp Leu Ser Val Leu Ala Leu Arg Glu Gly Arg Glu Ile Pro Pro Gly
        355                 360                 365

Asp Asp Pro Met Leu Leu Ala Tyr Leu Leu Asp Pro Gly Asn Thr Asn
    370                 375                 380

Pro Glu Gly Val Ala Arg Arg Tyr Gly Gly Glu Trp Lys Glu Asp Ala
385                 390                 395                 400

Ala Ala Arg Ala Leu Leu Ser Glu Arg Leu Trp Gln Ala Leu Tyr Pro
```

```
                405                 410                 415
Arg Val Ala Glu Glu Arg Leu Leu Trp Leu Tyr Arg Glu Val Glu
                420                 425                 430

Arg Pro Leu Ala Gln Val Leu Ala His Met Glu Ala Thr Gly Val Arg
                435                 440                 445

Leu Asp Val Pro Tyr Leu Glu Ala Leu Ser Gln Glu Val Ala Phe Glu
        450                 455                 460

Leu Glu Arg Leu Glu Ala Glu Val His Arg Leu Ala Gly His Pro Phe
465                 470                 475                 480

Asn Leu Asn Ser Arg Asp Gln Leu Arg Val Leu Phe Asp Glu Leu
                485                 490                 495

Gly Leu Pro Pro Ile Gly Lys Thr Glu Lys Thr Gly Lys Arg Ser Thr
                500                 505                 510

Ser Ala Ala Val Leu Glu Leu Leu Arg Glu Ala His Pro Ile Val Gly
                515                 520                 525

Arg Ile Leu Glu Tyr Arg Glu Leu Met Lys Leu Lys Ser Thr Tyr Ile
            530                 535                 540

Asp Pro Leu Pro Arg Leu Val His Pro Lys Thr Gly Arg Leu His Thr
545                 550                 555                 560

Arg Phe Asn Gln Thr Ala Thr Ala Thr Gly Arg Leu Ser Ser Ser Asp
                    565                 570                 575

Pro Asn Leu Gln Asn Ile Pro Val Arg Thr Pro Leu Gly Gln Arg Ile
                580                 585                 590

Arg Lys Ala Phe Ile Ala Glu Glu Gly His Leu Leu Val Ala Leu Asp
                595                 600                 605

Tyr Ser Gln Ile Glu Leu Arg Val Leu Ala His Leu Ser Gly Asp Glu
            610                 615                 620

Asn Leu Ile Arg Val Phe Arg Glu Gly Lys Asp Ile His Thr Glu Thr
625                 630                 635                 640

Ala Ala Trp Met Phe Gly Val Pro Pro Glu Gly Val Asp Gly Ala Met
                    645                 650                 655

Arg Arg Ala Ala Lys Thr Val Asn Tyr Gly Val Leu Tyr Gly Met Ser
                660                 665                 670

Ala His Arg Leu Ser Gln Glu Leu Ser Ile Pro Tyr Glu Glu Ala Ala
            675                 680                 685

Ala Phe Ile Glu Arg Tyr Phe Gln Ser Phe Pro Lys Val Arg Ala Trp
        690                 695                 700

Ile Ala Lys Thr Leu Glu Glu Gly Arg Lys Lys Gly Tyr Val Glu Thr
705                 710                 715                 720

Leu Phe Gly Arg Arg Arg Tyr Val Pro Asp Leu Asn Ala Arg Val Lys
                    725                 730                 735

Ser Val Arg Glu Ala Ala Glu Arg Met Ala Phe Asn Met Pro Val Gln
                740                 745                 750

Gly Thr Ala Ala Asp Leu Met Lys Leu Ala Met Val Lys Leu Phe Pro
            755                 760                 765

Arg Leu Arg Pro Leu Gly Val Arg Ile Leu Leu Gln Val His Asp Glu
        770                 775                 780

Leu Val Leu Glu Ala Pro Lys Ala Arg Ala Glu Glu Ala Ala Gln Leu
785                 790                 795                 800

Ala Lys Glu Thr Met Glu Gly Val Tyr Pro Leu Ser Val Pro Leu Glu
                805                 810                 815

Val Glu Val Gly Met Gly Glu Asp Trp Leu Ser Ala Lys Ala
                820                 825                 830
```

<210> SEQ ID NO 8
<211> LENGTH: 833
<212> TYPE: PRT
<213> ORGANISM: Thermus filiformis

<400> SEQUENCE: 8

```
Met Thr Pro Leu Phe Asp Leu Glu Glu Pro Lys Arg Val Leu Leu
1               5                   10                  15

Val Asp Gly His His Leu Ala Tyr Arg Thr Phe Tyr Ala Leu Ser Leu
            20                  25                  30

Thr Thr Ser Arg Gly Glu Pro Val Gln Met Val Tyr Gly Phe Ala Arg
        35                  40                  45

Ser Leu Leu Lys Ala Leu Lys Glu Asp Gly Gln Ala Val Val Val
50                  55                  60

Phe Asp Ala Lys Ala Pro Ser Phe Arg His Glu Ala Tyr Glu Ala Tyr
65                  70                  75                  80

Lys Ala Gly Arg Ala Pro Thr Pro Glu Asp Phe Pro Arg Gln Leu Ala
                85                  90                  95

Leu Val Lys Arg Leu Val Asp Leu Leu Gly Leu Val Arg Leu Glu Ala
            100                 105                 110

Pro Gly Tyr Glu Ala Asp Asp Val Leu Gly Thr Leu Ala Lys Lys Ala
        115                 120                 125

Glu Arg Glu Gly Met Glu Val Arg Ile Leu Thr Gly Asp Arg Asp Phe
130                 135                 140

Phe Gln Leu Leu Ser Lys Val Ser Val Leu Leu Pro Asp Gly Thr
145                 150                 155                 160

Leu Val Thr Pro Lys Asp Val Gln Glu Lys Tyr Gly Val Pro Pro Glu
                165                 170                 175

Arg Trp Val Asp Phe Arg Ala Leu Thr Gly Asp Arg Ser Asp Asn Ile
            180                 185                 190

Pro Gly Val Ala Gly Ile Gly Glu Lys Thr Ala Leu Arg Leu Leu Ala
        195                 200                 205

Glu Trp Gly Ser Val Glu Asn Leu Leu Lys Asn Leu Asp Arg Val Lys
210                 215                 220

Pro Asp Ser Val Arg Arg Lys Ile Glu Ala His Leu Glu Asp Leu Arg
225                 230                 235                 240

Leu Ser Leu Asp Leu Ala Arg Ile Arg Thr Asp Leu Pro Leu Glu Val
                245                 250                 255

Asp Phe Lys Ala Leu Arg Arg Thr Pro Asp Leu Glu Gly Leu Arg
            260                 265                 270

Ala Phe Leu Glu Glu Leu Glu Phe Gly Ser Leu Leu His Glu Phe Gly
        275                 280                 285

Leu Leu Gly Gly Glu Lys Pro Arg Glu Glu Ala Pro Trp Pro Pro
290                 295                 300

Glu Gly Ala Phe Val Gly Phe Leu Leu Ser Arg Lys Glu Pro Met Trp
305                 310                 315                 320

Ala Glu Leu Leu Ala Leu Ala Ala Ala Glu Gly Arg Val His Arg
                325                 330                 335

Ala Thr Ser Pro Val Glu Ala Leu Ala Asp Leu Lys Glu Ala Arg Gly
            340                 345                 350

Phe Leu Ala Lys Asp Leu Ala Val Leu Ala Leu Arg Glu Gly Val Ala
        355                 360                 365

Leu Asp Pro Thr Asp Asp Pro Leu Leu Val Ala Tyr Leu Leu Asp Pro
```

```
                370                 375                 380
Ala Asn Thr Asn Pro Glu Gly Val Ala Arg Arg Tyr Gly Gly Glu Phe
385                 390                 395                 400

Thr Glu Asp Ala Ala Glu Arg Ala Leu Leu Ser Glu Arg Leu Phe Gln
                405                 410                 415

Asn Leu Phe Pro Arg Leu Ser Glu Lys Leu Leu Trp Leu Tyr Gln Glu
                420                 425                 430

Val Glu Arg Pro Leu Ser Arg Val Leu Ala His Met Glu Ala Arg Gly
                435                 440                 445

Val Arg Leu Asp Val Pro Leu Leu Glu Ala Leu Ser Phe Glu Leu Glu
                450                 455                 460

Lys Glu Met Glu Arg Leu Gly Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Thr Pro Val Gly Arg Thr Glu Lys Thr Gly Lys Arg
                500                 505                 510

Ser Thr Ala Gln Gly Ala Leu Glu Ala Leu Arg Gly Ala His Pro Ile
                515                 520                 525

Val Glu Leu Ile Leu Gln Tyr Arg Glu Leu Ser Lys Leu Lys Ser Thr
                530                 535                 540

Tyr Leu Asp Pro Leu Pro Arg Leu Val His Pro Arg Thr Gly Arg Leu
545                 550                 555                 560

His Thr Arg Phe Asn Gln Thr Ala Thr Ala Thr Gly Arg Leu Ser Ser
                565                 570                 575

Ser Asp Pro Asn Leu Gln Asn Ile Pro Val Arg Thr Pro Leu Gly Gln
                580                 585                 590

Arg Ile Arg Lys Ala Phe Val Ala Glu Glu Gly Trp Leu Leu Leu Ala
                595                 600                 605

Ala Asp Tyr Ser Gln Ile Glu Leu Arg Val Leu Ala His Leu Ser Gly
                610                 615                 620

Asp Glu Asn Leu Lys Arg Val Phe Arg Glu Gly Lys Asp Ile His Thr
625                 630                 635                 640

Glu Thr Ala Ala Trp Met Phe Gly Leu Asp Pro Ala Leu Val Asp Pro
                645                 650                 655

Lys Met Arg Arg Ala Ala Lys Thr Val Asn Phe Gly Val Leu Tyr Gly
                660                 665                 670

Met Ser Ala His Arg Leu Ser Gln Glu Leu Gly Ile Asp Tyr Lys Glu
                675                 680                 685

Ala Glu Ala Phe Ile Glu Arg Tyr Phe Gln Ser Phe Pro Lys Val Arg
                690                 695                 700

Ala Trp Ile Glu Arg Thr Leu Glu Glu Gly Arg Thr Arg Gly Tyr Val
705                 710                 715                 720

Glu Thr Leu Phe Gly Arg Arg Arg Tyr Val Pro Asp Leu Ala Ser Arg
                725                 730                 735

Val Arg Ser Val Arg Glu Ala Ala Glu Arg Met Ala Phe Asn Met Pro
                740                 745                 750

Val Gln Gly Thr Ala Ala Asp Leu Met Lys Ile Ala Met Val Lys Leu
                755                 760                 765

Phe Pro Arg Leu Lys Pro Leu Gly Ala His Leu Leu Leu Gln Val His
                770                 775                 780

Asp Glu Leu Val Leu Glu Val Pro Glu Asp Arg Ala Glu Glu Ala Lys
785                 790                 795                 800
```

```
Ala Leu Val Lys Glu Val Met Glu Asn Thr Tyr Pro Leu Asp Val Pro
            805                 810                 815

Leu Glu Val Glu Val Gly Val Gly Arg Asp Trp Leu Glu Ala Lys Gly
            820                 825                 830

Asp

<210> SEQ ID NO 9
<211> LENGTH: 893
<212> TYPE: PRT
<213> ORGANISM: Thermotoga maritima

<400> SEQUENCE: 9

Met Ala Arg Leu Phe Leu Phe Asp Gly Thr Ala Leu Ala Tyr Arg Ala
1               5                   10                  15

Tyr Tyr Ala Leu Asp Arg Ser Leu Ser Thr Ser Thr Gly Ile Pro Thr
            20                  25                  30

Asn Ala Thr Tyr Gly Val Ala Arg Met Leu Val Arg Phe Ile Lys Asp
        35                  40                  45

His Ile Ile Val Gly Lys Asp Tyr Val Ala Val Ala Phe Asp Lys Lys
    50                  55                  60

Ala Ala Thr Phe Arg His Lys Leu Leu Glu Thr Tyr Lys Ala Gln Arg
65                  70                  75                  80

Pro Lys Thr Pro Asp Leu Leu Ile Gln Gln Leu Pro Tyr Ile Lys Lys
                85                  90                  95

Leu Val Glu Ala Leu Gly Met Lys Val Leu Glu Val Glu Gly Tyr Glu
            100                 105                 110

Ala Asp Asp Ile Ile Ala Thr Leu Ala Val Lys Gly Leu Pro Leu Phe
        115                 120                 125

Asp Glu Ile Phe Ile Val Thr Gly Asp Lys Asp Met Leu Gln Leu Val
    130                 135                 140

Asn Glu Lys Ile Lys Val Trp Arg Ile Val Lys Gly Ile Ser Asp Leu
145                 150                 155                 160

Glu Leu Tyr Asp Ala Gln Lys Val Lys Glu Lys Tyr Gly Val Glu Pro
                165                 170                 175

Gln Gln Ile Pro Asp Leu Leu Ala Leu Thr Gly Asp Glu Ile Asp Asn
            180                 185                 190

Ile Pro Gly Val Thr Gly Ile Gly Glu Lys Thr Ala Val Gln Leu Leu
        195                 200                 205

Glu Lys Tyr Lys Asp Leu Glu Asp Ile Leu Asn His Val Arg Glu Leu
    210                 215                 220

Pro Gln Lys Val Arg Lys Ala Leu Leu Arg Asp Arg Glu Asn Ala Ile
225                 230                 235                 240

Leu Ser Lys Lys Leu Ala Ile Leu Glu Thr Asn Val Pro Ile Glu Ile
                245                 250                 255

Asn Trp Glu Glu Leu Arg Tyr Gln Gly Tyr Asp Arg Gly Lys Leu Leu
            260                 265                 270

Pro Leu Leu Lys Glu Leu Glu Phe Ala Ser Ile Met Lys Glu Leu Gln
        275                 280                 285

Leu Tyr Glu Glu Ser Glu Pro Val Gly Tyr Arg Ile Val Lys Asp Leu
    290                 295                 300

Val Glu Phe Glu Lys Leu Ile Glu Lys Leu Arg Glu Ser Pro Ser Phe
305                 310                 315                 320

Ala Ile Asp Leu Glu Thr Ser Ser Leu Asp Pro Phe Asp Cys Asp Ile
                325                 330                 335
```

```
Val Gly Ile Ser Val Ser Phe Lys Pro Lys Glu Ala Tyr Tyr Ile Pro
            340                 345                 350

Leu His His Arg Asn Ala Gln Asn Leu Asp Glu Lys Glu Val Leu Lys
            355                 360                 365

Lys Leu Lys Glu Ile Leu Glu Asp Pro Gly Ala Lys Ile Val Gly Gln
370                 375                 380

Asn Leu Lys Phe Asp Tyr Lys Val Leu Met Val Lys Gly Val Glu Pro
385                 390                 395                 400

Val Pro Pro Tyr Phe Asp Thr Met Ile Ala Ala Tyr Leu Leu Glu Pro
            405                 410                 415

Asn Glu Lys Lys Phe Asn Leu Asp Asp Leu Ala Leu Lys Phe Leu Gly
            420                 425                 430

Tyr Lys Met Thr Ser Tyr Gln Glu Leu Met Ser Phe Ser Phe Pro Leu
            435                 440                 445

Phe Gly Phe Ser Phe Ala Asp Val Pro Val Glu Lys Ala Ala Asn Tyr
450                 455                 460

Ser Cys Glu Asp Ala Asp Ile Thr Tyr Arg Leu Tyr Lys Thr Leu Ser
465                 470                 475                 480

Leu Lys Leu His Glu Ala Asp Leu Glu Asn Val Phe Tyr Lys Ile Glu
            485                 490                 495

Met Pro Leu Val Asn Val Leu Ala Arg Met Glu Leu Asn Gly Val Tyr
            500                 505                 510

Val Asp Thr Glu Phe Leu Lys Lys Leu Ser Glu Glu Tyr Gly Lys Lys
            515                 520                 525

Leu Glu Glu Leu Ala Glu Glu Ile Tyr Arg Ile Ala Gly Glu Pro Phe
            530                 535                 540

Asn Ile Asn Ser Pro Lys Gln Val Ser Arg Ile Leu Phe Glu Lys Leu
545                 550                 555                 560

Gly Ile Lys Pro Arg Gly Lys Thr Thr Lys Thr Gly Asp Tyr Ser Thr
            565                 570                 575

Arg Ile Glu Val Leu Glu Glu Leu Ala Gly Glu His Glu Ile Ile Pro
            580                 585                 590

Leu Ile Leu Glu Tyr Arg Lys Ile Gln Lys Leu Lys Ser Thr Tyr Ile
            595                 600                 605

Asp Ala Leu Pro Lys Met Val Asn Pro Lys Thr Gly Arg Ile His Ala
            610                 615                 620

Ser Phe Asn Gln Thr Gly Thr Ala Thr Gly Arg Leu Ser Ser Ser Asp
625                 630                 635                 640

Pro Asn Leu Gln Asn Leu Pro Thr Lys Ser Glu Gly Lys Glu Ile
            645                 650                 655

Arg Lys Ala Ile Val Pro Gln Asp Pro Asn Trp Trp Ile Val Ser Ala
            660                 665                 670

Asp Tyr Ser Gln Ile Glu Leu Arg Ile Leu Ala His Leu Ser Gly Asp
            675                 680                 685

Glu Asn Leu Leu Arg Ala Phe Glu Glu Gly Ile Asp Val His Thr Leu
            690                 695                 700

Thr Ala Ser Arg Ile Phe Asn Val Lys Pro Glu Glu Val Thr Glu Glu
705                 710                 715                 720

Met Arg Arg Ala Gly Lys Met Val Asn Phe Ser Ile Ile Tyr Gly Val
            725                 730                 735

Thr Pro Tyr Gly Leu Ser Val Arg Leu Gly Val Pro Val Lys Glu Ala
            740                 745                 750
```

```
Glu Lys Met Ile Val Asn Tyr Phe Val Leu Tyr Pro Lys Val Arg Asp
            755                 760                 765

Tyr Ile Gln Arg Val Val Ser Glu Ala Lys Lys Gly Tyr Val Arg
770                 775                 780

Thr Leu Phe Gly Arg Lys Arg Asp Ile Pro Gln Leu Met Ala Arg Asp
785                 790                 795                 800

Arg Asn Thr Gln Ala Glu Gly Glu Arg Ile Ala Ile Asn Thr Pro Ile
            805                 810                 815

Gln Gly Thr Ala Ala Asp Ile Ile Leu Ala Met Ile Glu Ile Asp
            820                 825                 830

Arg Glu Leu Lys Glu Arg Lys Met Arg Ser Lys Met Ile Ile Gln Val
            835                 840                 845

His Asp Glu Leu Val Phe Glu Val Pro Asn Glu Glu Lys Asp Ala Leu
            850                 855                 860

Val Glu Leu Val Lys Asp Arg Met Thr Asn Val Val Lys Leu Ser Val
865                 870                 875                 880

Pro Leu Glu Val Asp Val Thr Ile Gly Lys Thr Trp Ser
            885                 890
```

<210> SEQ ID NO 10
<211> LENGTH: 893
<212> TYPE: PRT
<213> ORGANISM: Thermotoga neapolitana

<400> SEQUENCE: 10

```
Met Ala Arg Leu Phe Leu Phe Asp Gly Thr Ala Leu Ala Tyr Arg Ala
1               5                   10                  15

Tyr Tyr Ala Leu Asp Arg Ser Leu Ser Thr Ser Thr Gly Ile Pro Thr
                20                  25                  30

Asn Ala Val Tyr Gly Val Ala Arg Met Leu Val Lys Phe Ile Lys Glu
            35                  40                  45

His Ile Ile Pro Glu Lys Asp Tyr Ala Ala Val Ala Phe Asp Lys Lys
        50                  55                  60

Ala Ala Thr Phe Arg His Lys Leu Leu Glu Ala Tyr Lys Ala Gln Arg
65                  70                  75                  80

Pro Lys Thr Pro Asp Leu Leu Val Gln Gln Leu Pro Tyr Ile Lys Arg
                85                  90                  95

Leu Ile Glu Ala Leu Gly Phe Lys Val Leu Glu Leu Glu Gly Tyr Glu
            100                 105                 110

Ala Asp Asp Ile Ile Ala Thr Leu Ala Val Lys Gly Cys Thr Phe Phe
        115                 120                 125

Asp Glu Ile Phe Ile Ile Thr Gly Asp Lys Asp Met Leu Gln Leu Val
130                 135                 140

Asn Glu Lys Ile Lys Val Trp Arg Ile Val Lys Gly Ile Ser Asp Leu
145                 150                 155                 160

Glu Leu Tyr Asp Ser Lys Lys Val Lys Glu Arg Tyr Gly Val Glu Pro
                165                 170                 175

His Gln Ile Pro Asp Leu Leu Ala Leu Thr Gly Asp Glu Ile Asp Asn
            180                 185                 190

Ile Pro Gly Val Thr Gly Ile Gly Glu Lys Thr Ala Val Gln Leu Leu
        195                 200                 205

Gly Lys Tyr Arg Asn Leu Glu Asp Ile Leu Glu His Ala Arg Glu Leu
210                 215                 220

Pro Gln Arg Val Arg Lys Ala Leu Leu Arg Asp Arg Glu Val Ala Ile
225                 230                 235                 240
```

```
Leu Ser Lys Lys Leu Ala Thr Leu Val Thr Asn Ala Pro Val Glu Val
            245                 250                 255

Asp Trp Glu Glu Met Lys Tyr Arg Gly Tyr Asp Lys Arg Lys Leu Leu
            260                 265                 270

Pro Ile Leu Lys Glu Leu Glu Phe Ala Ser Ile Met Lys Glu Leu Gln
            275                 280                 285

Leu Tyr Glu Glu Ala Glu Pro Thr Gly Tyr Glu Ile Val Lys Asp His
            290                 295                 300

Lys Thr Phe Glu Asp Leu Ile Glu Lys Leu Lys Glu Val Pro Ser Phe
305                 310                 315                 320

Ala Leu Asp Leu Glu Thr Ser Ser Leu Asp Pro Phe Asn Cys Glu Ile
            325                 330                 335

Val Gly Ile Ser Val Ser Phe Lys Pro Lys Thr Ala Tyr Tyr Ile Pro
            340                 345                 350

Leu His His Arg Asn Ala Gln Asn Leu Asp Glu Thr Leu Val Leu Ser
            355                 360                 365

Lys Leu Lys Glu Ile Leu Glu Asp Pro Ser Ser Lys Ile Val Gly Gln
            370                 375                 380

Asn Leu Lys Tyr Asp Tyr Lys Val Leu Met Val Lys Gly Ile Ser Pro
385                 390                 395                 400

Val Tyr Pro His Phe Asp Thr Met Ile Ala Ala Tyr Leu Leu Glu Pro
            405                 410                 415

Asn Glu Lys Lys Phe Asn Leu Glu Asp Leu Ser Leu Lys Phe Leu Gly
            420                 425                 430

Tyr Lys Met Thr Ser Tyr Gln Glu Leu Met Ser Phe Ser Ser Pro Leu
            435                 440                 445

Phe Gly Phe Ser Phe Ala Asp Val Pro Val Asp Lys Ala Ala Asn Tyr
            450                 455                 460

Ser Cys Glu Asp Ala Asp Ile Thr Tyr Arg Leu Tyr Lys Ile Leu Ser
465                 470                 475                 480

Met Lys Leu His Glu Ala Leu Glu Asn Val Phe Tyr Arg Ile Glu
            485                 490                 495

Met Pro Leu Val Asn Val Leu Ala Arg Met Glu Leu Asn Gly Val Tyr
            500                 505                 510

Val Asp Thr Glu Phe Leu Lys Lys Leu Ser Glu Glu Tyr Gly Lys Lys
            515                 520                 525

Leu Glu Glu Leu Ala Glu Lys Ile Tyr Gln Ile Ala Gly Glu Pro Phe
            530                 535                 540

Asn Ile Asn Ser Pro Lys Gln Val Ser Lys Ile Leu Phe Glu Lys Leu
545                 550                 555                 560

Gly Ile Lys Pro Arg Gly Lys Thr Thr Lys Thr Gly Glu Tyr Ser Thr
            565                 570                 575

Arg Ile Glu Val Leu Glu Glu Ile Ala Asn Glu His Glu Ile Val Pro
            580                 585                 590

Leu Ile Leu Glu Tyr Arg Lys Ile Gln Lys Leu Lys Ser Thr Tyr Ile
            595                 600                 605

Asp Thr Leu Pro Lys Leu Val Asn Pro Lys Thr Gly Arg Ile His Ala
            610                 615                 620

Ser Phe His Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
            645                 650                 655
```

```
Arg Lys Ala Ile Val Pro Gln Asp Pro Asp Trp Trp Ile Val Ser Ala
                660                 665                 670

Asp Tyr Ser Gln Ile Glu Leu Arg Ile Leu Ala His Leu Ser Gly Asp
            675                 680                 685

Glu Asn Leu Val Lys Ala Phe Glu Glu Gly Ile Asp Val His Thr Leu
        690                 695                 700

Thr Ala Ser Arg Ile Tyr Asn Val Lys Pro Glu Glu Val Asn Glu Glu
705                 710                 715                 720

Met Arg Arg Val Gly Lys Met Val Asn Phe Ser Ile Ile Tyr Gly Val
                725                 730                 735

Thr Pro Tyr Gly Leu Ser Val Arg Leu Gly Ile Pro Val Lys Glu Ala
            740                 745                 750

Glu Lys Met Ile Ile Ser Tyr Phe Thr Leu Tyr Pro Lys Val Arg Ser
        755                 760                 765

Tyr Ile Gln Gln Val Val Ala Glu Ala Lys Glu Lys Gly Tyr Val Arg
770                 775                 780

Thr Leu Phe Gly Arg Lys Arg Asp Ile Pro Gln Leu Met Ala Arg Asp
785                 790                 795                 800

Lys Asn Thr Gln Ser Glu Gly Glu Arg Ile Ala Ile Asn Thr Pro Ile
                805                 810                 815

Gln Gly Thr Ala Ala Asp Ile Ile Lys Leu Ala Met Ile Asp Ile Asp
            820                 825                 830

Glu Glu Leu Arg Lys Arg Asn Met Lys Ser Arg Met Ile Ile Gln Val
        835                 840                 845

His Asp Glu Leu Val Phe Glu Val Pro Asp Glu Glu Lys Glu Glu Leu
850                 855                 860

Val Asp Leu Val Lys Asn Lys Met Thr Asn Val Val Lys Leu Ser Val
865                 870                 875                 880

Pro Leu Glu Val Asp Ile Ser Ile Gly Lys Ser Trp Ser
                885                 890

<210> SEQ ID NO 11
<211> LENGTH: 832
<212> TYPE: PRT
<213> ORGANISM: Artficial
<220> FEATURE:
<223> OTHER INFORMATION: Synthetic

<400> SEQUENCE: 11

Met Arg Gly Met Leu Pro Leu Phe Glu Pro Lys Gly Arg Val Leu Leu
1               5                   10                  15

Val Asp Gly His His Leu Ala Tyr Arg Thr Phe His Ala Leu Lys Gly
                20                  25                  30

Leu Thr Thr Ser Arg Gly Glu Pro Val Gln Ala Val Tyr Gly Phe Ala
            35                  40                  45

Lys Ser Leu Leu Lys Ala Leu Lys Glu Asp Trp Asp Ala Val Ile Val
        50                  55                  60

Val Phe Asp Ala Lys Ala Pro Ser Phe Arg His Glu Ala Tyr Gly Gly
65                  70                  75                  80

Tyr Lys Ala Gly Arg Ala Pro Thr Pro Glu Asp Phe Pro Arg Gln Leu
                85                  90                  95

Ala Leu Ile Lys Glu Leu Val Asp Leu Leu Gly Leu Ala Arg Leu Glu
            100                 105                 110

Val Pro Gly Tyr Glu Ala Asp Asp Val Leu Ala Ser Leu Ala Lys Lys
        115                 120                 125
```

-continued

Ala Glu Lys Glu Gly Tyr Glu Val Arg Ile Leu Thr Ala Asp Lys Asp
    130                 135                 140

Leu Tyr Gln Leu Leu Ser Asp Arg Ile His Ile Leu His Pro Glu Gly
145                 150                 155                 160

Tyr Leu Ile Thr Pro Ala Trp Leu Trp Glu Lys Tyr Gly Leu Arg Pro
                165                 170                 175

Asp Gln Trp Ala Asp Tyr Arg Ala Leu Thr Gly Asp Glu Ser Asp Asn
            180                 185                 190

Leu Pro Gly Val Lys Gly Ile Gly Glu Lys Thr Ala Arg Lys Leu Leu
        195                 200                 205

Glu Glu Trp Gly Ser Leu Glu Ala Leu Leu Lys Asn Leu Asp Arg Leu
    210                 215                 220

Lys Pro Ala Ile Arg Glu Lys Ile Leu Ala His Met Asp Asp Leu Lys
225                 230                 235                 240

Leu Ser Trp Asp Met Ala Lys Val Arg Thr Asp Leu Pro Leu Glu Val
                245                 250                 255

Asp Phe Ala Lys Arg Arg Glu Pro Asp Arg Glu Arg Leu Arg Ala Phe
            260                 265                 270

Leu Glu Arg Leu Glu Phe Gly Ser Leu Leu His Glu Phe Gly Leu Leu
    275                 280                 285

Glu Ser Pro Lys Ala Leu Glu Glu Ala Pro Trp Pro Pro Pro Glu Gly
    290                 295                 300

Ala Phe Val Gly Phe Val Leu Ser Arg Lys Glu Pro Met Trp Ala Asp
305                 310                 315                 320

Leu Leu Ala Leu Ala Ala Arg Gly Gly Arg Val His Arg Ala Pro
                325                 330                 335

Glu Pro Tyr Lys Ala Leu Arg Asp Leu Lys Glu Ala Arg Gly Leu Leu
            340                 345                 350

Ala Lys Asp Leu Ser Val Leu Ala Leu Arg Glu Gly Leu Gly Leu Pro
        355                 360                 365

Pro Gly Asp Asp Pro Met Leu Leu Ala Tyr Leu Leu Asp Pro Ser Asn
    370                 375                 380

Thr Thr Pro Glu Gly Val Ala Arg Arg Tyr Gly Gly Glu Trp Thr Glu
385                 390                 395                 400

Glu Ala Gly Glu Arg Ala Ala Leu Ser Glu Arg Leu Phe Ala Asn Leu
                405                 410                 415

Trp Gly Arg Leu Glu Gly Glu Glu Arg Leu Leu Trp Leu Tyr Arg Glu
            420                 425                 430

Val Glu Arg Pro Leu Ser Ala Val Leu Ala His Met Glu Ala Thr Gly
        435                 440                 445

Val Arg Leu Asp Val Ala Tyr Leu Arg Ala Leu Ser Leu Glu Val Ala
    450                 455                 460

Glu Glu Ile Ala Arg Leu Glu Ala Glu Val Phe Arg Leu Ala Gly His
465                 470                 475                 480

Pro Phe Asn Leu Asn Ser Arg Asp Gln Leu Glu Arg Val Leu Phe Asp
                485                 490                 495

Glu Leu Gly Leu Pro Ala Ile Gly Lys Thr Lys Thr Gly Lys Arg
            500                 505                 510

Ser Thr Ser Ala Ala Val Leu Glu Ala Leu Arg Glu Ala His Pro Ile
        515                 520                 525

Val Glu Lys Ile Leu Gln Tyr Arg Glu Leu Thr Lys Leu Lys Ser Thr
    530                 535                 540

Tyr Ile Asp Pro Leu Pro Asp Leu Ile His Pro Arg Thr Gly Arg Leu

His Thr Arg Phe Asn Gln Thr Ala Thr Ala Thr Gly Arg Leu Ser Ser
545                 550                 555                 560

Ser Asp Pro Asn Leu Gln Asn Ile Pro Val Arg Thr Pro Leu Gly Gln
            565                 570                 575

Arg Ile Arg Arg Ala Phe Ile Ala Glu Glu Gly Trp Leu Val Ala
        580                 585                 590

Leu Asp Tyr Ser Gln Ile Glu Leu Arg Val Leu Ala His Leu Ser Gly
    595                 600                 605

Asp Glu Asn Leu Ile Arg Val Phe Gln Glu Gly Arg Asp Ile His Thr
610                 615                 620

Glu Thr Ala Ser Trp Met Phe Gly Val Pro Arg Glu Ala Val Asp Pro
625                 630                 635                 640

Leu Met Arg Ala Ala Lys Thr Ile Asn Phe Gly Val Leu Tyr Gly
        645                 650                 655

Met Ser Ala His Arg Leu Ser Gln Glu Leu Ala Ile Pro Tyr Glu Glu
        660                 665                 670

Ala Gln Ala Phe Ile Glu Arg Tyr Phe Gln Ser Phe Pro Lys Val Arg
    675                 680                 685

Ala Trp Ile Glu Lys Thr Leu Glu Glu Gly Arg Arg Arg Gly Tyr Val
690                 695                 700

Glu Thr Leu Phe Gly Arg Arg Tyr Val Pro Asp Leu Glu Ala Arg
705                 710                 715                 720

Val Lys Ser Val Arg Glu Ala Ala Glu Arg Met Ala Ile Asn Met Pro
        725                 730                 735

Val Gln Gly Thr Ala Ala Asp Leu Met Lys Leu Ala Met Val Lys Leu
        740                 745                 750

Phe Pro Arg Leu Glu Glu Met Gly Ala Arg Met Leu Leu Gln Val His
    755                 760                 765

Asp Glu Leu Val Leu Glu Ala Pro Lys Glu Arg Ala Glu Ala Val Ala
785                 770                 775                 780

Arg Leu Ala Lys Glu Val Met Glu Gly Val Tyr Pro Leu Ala Val Pro
            805                 810                 815

Leu Glu Val Glu Val Gly Ile Gly Glu Asp Trp Leu Ser Ala Lys Glu
                820                 825                 830

<210> SEQ ID NO 12
<211> LENGTH: 2499
<212> TYPE: DNA
<213> ORGANISM: Artificial
<220> FEATURE:
<223> OTHER INFORMATION: Synthetic

<400> SEQUENCE: 12
atgcgtggca tgcttcctct ttttgagccc aagggccggg tcctcctggt ggacggccac      60
cacctggcct accgcacctt ccacgccctg aagggcctca ccaccagccg ggggagccg      120 gtgcaggcgg tctacggctt cgccaagagc ctcctcaagg ccctcaagga ggactgggac      180
gcggtgatcg tggtctttga cgccaaggcc cctccttcc gccacgaggc ctacgggggg      240
tacaaggcgg ccgggccccc cacgccgag  gactttcccc ggcaactcgc cctcatcaag      300
gagctggtgg acctcctggg gctggcgcgc tcgaggtcc cgggctacga ggcggacgac      360
gtcctggcca gctggccaa gaaggcggaa aaggagggct acgaggtccg catcctcacc      420
gccgacaaag acctttacca gctccttccc gaccgcatcc acatcctcca ccccgagggg      480

```
tacctcatca ccccggcctg gctttgggaa aagtacggcc tgaggcccga ccagtgggcc      540
gactaccggg ccctgaccgg ggacgagtcc gacaaccttc ccggggtcaa gggcatcggg      600
gagaagacgg cgaggaagct tctggaggag tgggggagcc tggaagccct cctcaagaac      660
ctggaccggc tgaagcccgc catccggag aagatcctgg cccacatgga cgatctgaag       720
ctctcctggg acatggccaa ggtgcgcacc gacctgcccc tggaggtgga cttcgccaaa      780
aggcgggagc ccgaccggga gaggcttagg gcctttctgg agaggcttga gtttggcagc      840
ctcctccacg agttcggcct tctggaaagc cccaaggccc tggaggaggc cccctggccc      900
ccgccggaag gggccttcgt gggctttgtg ctttcccgca aggagcccat gtgggccgat      960
cttctggccc tggccgccgc caggggggc cgggtccacc gggcccccga gccttataaa      1020
gccctcaggg acctgaagga ggcgcggggg cttctcgcca aagacctgag cgttctggcc     1080
ctgagggaag gccttggcct cccgcccggc gacgacccca tgctcctcgc ctacctcctg     1140
gacccttcca acaccacccc cgagggggtg gcccggcgct acggcgggga gtggacggag     1200
gaggcggggg agcgggccgc cctttccgag aggctcttcg ccaacctgtg ggggaggctt     1260 gaggggagg agaggctcct ttggctttac cgggaggtgg agaggcccct ttccgctgtc      1320
ctggcccaca tggaggccac gggggtgcgc ctggacgtgg cctatctcag ggccttgtcc     1380
ctggaggtgg ccgaggagat cgcccgcctc gaggccgagg tcttccgcct ggccggccac     1440
cccttcaacc tcaactcccg ggaccagctg gaaagggtcc tctttgacga gctagggctt     1500
cccgccatcg gcaagacgaa gaagaccggc aagcgctcca ccagcgccgc cgtcctggag     1560
gccctccgcg aggcccaccc catcgtggag aagatcctgc agtaccggga gctcaccaag     1620
ctgaagagca cctacattga ccccttgccg gacctcatcc accccaggac gggccgcctc     1680
cacacccgct tcaaccagac ggccacggcc acgggcaggc taagtagctc cgatcccaac     1740
ctccagaaca tccccgtccg cacccccgctt gggcagagga tccgccgggc cttcatcgcc     1800
gaggaggggt ggctattggt ggccctggac tatagccaga tagagctcag ggtgctggcc     1860
cacctctccg gcgacgagaa cctgatccgg gtcttccagg aggggcggga catccacacg     1920
gagaccgcca gctggatgtt cggcgtcccc cgggaggccg tggacccccct gatgcgccgg     1980 gcggccaaga ccatcaactt cggggtcctc tacggcatgt cggcccaccg cctctcccag     2040
gagctagcca tccttacga ggaggcccag gccttcattg agcgctactt tcagagcttc      2100
cccaaggtgc gggcctggat tgagaagacc ctggaggagg gcaggaggcg ggggtacgtg     2160
gagaccctct tcggccgccg ccgctacgtg ccagacctag aggcccgggt gaagagcgtg     2220
cgggaggcgg ccgagcgcat ggccatcaac atgcccgtcc agggcaccgc cgccgacctc     2280
atgaagctgg ctatggtgaa gctcttcccc aggctggagg aaatggggc caggatgctc     2340 cttcaggtcc acgacgagct ggtcctcgag gccccaaaag agagggcgga ggccgtggcc     2400
cggctggcca aggaggtcat ggagggggtg tatccctgg ccgtgcccct ggaggtggag     2460
gtggggatag gggaggactg gctctccgcc aaggagtaa                            2499
```

THERMOSTABLE TYPE-A DNA POLYMERASE MUTANT WITH INCREASED RESISTANCE TO INHIBITORS IN BLOOD

CROSS REFERENCE TO RELATED APPLICATION

This application claims priority of U.S. Provisional Application No. 61/940,172 filed on Feb. 14, 2014. The content of the application is incorporated herein by reference in its entirety.

FIELD OF THE INVENTION

This invention relates to the field of molecular biology. More specifically, the invention relates to improved polymerases for performing Polymerase Chain Reactions (PCR) and to methods of performing PCR.

BACKGROUND OF THE INVENTION

PCR is one of the most widely used nucleic acid detection methods. It has various applications in the fields of research and molecular diagnosis of infectious diseases and genetic disorders. Among the many applications, blood-based PCR diagnoses are particularly ire demand.

On the one hand, the blood is a vital part of the circulatory system for the human body. It includes many types of host cells, including normal cells, diseased cells (e.g., circulating tumor cells), and, if the host is a pregnant mother, fetal cells, as well as genetic materials from such cells, such as microRNAs. Indeed, due to the minimum invasive nature, blood-based PCR is advantageous in some situations such as foetal diagnosis using a maternal blood sample without the risk of abortion associated with conventional amniotic fluid tests. Under certain circumstances, the blood also contains pathogens, such as viruses and bacteria. Accordingly, blood-based diagnoses can provide an immediate picture of what is happening in the human body at any given time. On the other hand, blood is the source for various pharmaceutical and blood products (e.g., whole blood, plasma, antibodies, and stem cells) that are used to improve the quality of life and to save lives in a variety of traumatic or pathological situations. These therapeutic uses of blood, plasma, and other blood-derived materials require that donations of these materials be as free as possible from contamination of diseased cells (e.g., tumor cells) or pathogens (e.g., HIV, HBV, and HCV). See, e.g., US Applications 20130316925, 20130157253, 20120329061, 20120070827, 20120034614, 20070281307, and 20070105121.

However, blood-based PCR diagnoses have been limited by a number of logistic and technical challenges. The challenges associated with nucleic acid diagnostics from biological samples are many folds. Complex biological samples, such as blood and cell lysates, have various components that can inhibit DNA polymerases used in PCR reactions. These components include hemoglobin, immunoglobulin G, lactoferrin, and proteases in blood. Although various procedures have been developed to purify samples before attempting PCR reactions, these steps are generally time-consuming, labor-intensive, and might not achieve the purification required for the subsequent PCR. In addition, nucleic acid-containing cells (e.g., white blood cells and fetal cells) account for only a small fraction of a blood sample, precious nucleic acid can be lost from the sample before the PCR reaction step.

When working with blood, one key point is that a blood sample should be collected in anticoagulants to prevent clotting since isolation of nucleic acids from clotted blood is not efficient and most of the cells will be lost in the clot. However, anticoagulants routinely used in blood sample collection, such as EDTA and heparin, interfere with or inhibit PCR. For example, heparin is highly negatively charged and will co-extract with DNA and thereby inhibit PCR reactions. See e.g., Garcia et al. J. Clin. Microbiol. April 2002 vol. 40 no. 4 1567-1568, and Yokota et al., Journal of Clinical Laboratory Analysis, Volume 13, Issue 3, pages 133-140, 1999.

Thus, there is a need for reagents, such as DNA polymerases, that are more resistant to the above-mentioned inhibitors and suitable for PCR reactions using blood samples.

SUMMARY OF INVENTION

This invention relates to thermostable Type A DNA polymerase mutants that have increased resistance to inhibitors in whole blood, which include natural components of blood (hemoglobin in erythrocytes, lactoferrin in leukocytes) or plasma (immunoglobulin G), or added anticoagulants, such as EDTA and heparin.

Accordingly, in one aspect, the invention provides an isolated, mutant thermostable Type-A DNA polymerase. The mutant polymerase comprises, consists essentially of, or consists of a first mutation at residue 507 of a wild-type Taq DNA polymerase (SEQ ID NO: 4) or at a residue corresponding to residue 507 of the wild-type Taq DNA polymerase in another thermostable Type-A DNA polymerase; and additional mutations at residues 59, 155, 245, and 749 of the wild-type Taq DNA polymerase, or at corresponding residues in the another thermostable Type-A DNA polymerase. The mutant polymerase possesses (i) DNA polymerase activity and (ii) a higher resistance to a polymerization activity inhibitor (e.g., natural components of blood or anticoagulants such as EDTA or heparin) than the wild-type DNA polymerase from which it is derived. The mutant polymerase is free of mutation at residue 375 or 734 of the wild-type Taq DNA polymerase, or at corresponding residues in the another thermostable Type-A DNA polymerase. The mutant can also possess a faster polymerization rate as compared with the wild-type DNA polymerase.

In some embodiments, the wild-type Type-A DNA polymerase comprises, consists essentially of, or consists of a sequence selected from the group consisting of SEQ ID NOs: 1-10. The mutant DNA polymerase is at least 70% (e.g., 75, 80, 85, 90, 95, 96, 97, 98, or 99%) identical to a sequence selected from the group consisting of SEQ ID NOs: 1-10. In one example, the wild-type Taq DNA polymerase comprises, consists essentially of, or consists of the sequence of SEQ ID NO: 4. In other words, the mutant polymerase is a mutant Taq DNA polymerase.

In a preferred embodiment, the first mutation in the mutant is an E507K mutation based on the sequence of SEQ ID NO: 4. In a more preferred embodiment, the mutant contains the following five mutations: G59W, V155I, L245M, E507K, and F749I. For example, the mutant can be one comprising, consisting essentially of, or consisting of the sequence of SEQ ID NO: 11. In other embodiments, the mutant can be a DNA polymerase that has the above-described five mutations and is at least 70% (e.g., 75, 80, 85, 90, 95, 96, 97, 98, or 99%) identical to the sequence of SEQ ID NO: 11.

The invention further provides a composition (e.g., a master mix for PCR reactions) comprising (i) the mutant DNA polymerase described above and (ii) one or more reagents selected from the group consisting of an aqueous buffer, a divalent metal (e.g., magnesium), extension nucleotides, primers, a detergent, a detection agent (e.g., specific or non-specific dyes or fluorescent molecules), and a target nucleic acid template. Also provided is a kit containing the mutant DNA polymerase or composition described above, and packaging materials therefor. The kit can include one or more reagents selected from the group consisting of an aqueous buffer, a divalent metal, an extension nucleotide, a primer, a probe, a detergent, a detection agent, a dye, a fluorescent molecule, an anticoagulant, and a cell lysis agent.

The above-described mutant DNA polymerase can be used in a method of primer-extending or a method of amplifying a target nucleic acid. The method includes the steps of: providing a test sample (e.g., a blood sample) suspected of containing the target nucleic acid; contacting the test sample with the mutant polymerase, a primer that specifically binds or hybridizes to a strand of the target nucleic acid, and extension nucleotides to form a mixture; and incubating the mixture under conditions permitting extension of the primer by the polymerase using the sequence of the target nucleic acid as a template for incorporation of the extension nucleotides. The method can be a method of PCR, and in that case, a second primer that specifically binds or hybridizes to the complement of the target nucleic acid strand mentioned above can be used. The test sample can be a blood sample, which can account for at least 1% (2%, 5%, 10%, 20%, 25%, 30%, 35%, 40%, 45%, or 50%) v/v of the mixture.

The above-described mutant DNA polymerases, compositions (e.g., master mixes for PCR reactions), and methods are particularly useful for blood sample-based PCR reactions. For example, they can be used for real-time PCR from whole blood spotted on Guthrie cards (with no anticoagulants) or from plasma, which is made from whole blood treated with anticoagulants by removing cells by centrifugation. In this application, the whole blood samples can be partially purified (by attachment to Guthrie cards or by centrifugation to remove red blood cells) to remove heme and other factors that quench florescence detection.

Another aspect of this invention provides an isolated nucleic acid that encodes the above-mentioned mutant DNA polymerase polypeptide. The nucleic acid can contain a sequence that is at least 70% (e.g., 80, 85, 90, 95, or 99%) identical to SEQ ID NO: 12. The invention also provides a vector, such as an expression vector, comprising the nucleic acid and a host cell comprising the nucleic acid. The nucleic acid, vector, and host cell can be used for producing a mutant DNA polymerase polypeptide of this invention. Accordingly, this invention also provides a method for producing the polypeptide. The method includes culturing the host cell in a medium under conditions permitting expression of a polypeptide encoded by the nucleic acid, and purifying the polypeptide from the cultured cell or the medium of the cell.

The details of one or more embodiments of the invention are set forth in the description below. Other features, objectives, and advantages of the invention will be apparent from the description and from the claims.

BRIEF DESCRIPTION OF THE DRAWINGS

FIG. 1 shows an alignment of exemplary thermostable Type-A DNA polymerases that can be mutated to create an engineered DNA polymerase according to the invention.

FIG. 3A shows results with 2.5% v/v EDTA-treated whole blood; FIG. 3B shows results with 25% v/v EDTA-treated whole blood; FIG. 3C shows results with 45% v/v EDTA-treated whole blood.

FIG. 4A shows results with 2.5% v/v heparin-treated whole blood; FIG. 4B shows results with 25% v/v heparin-treated whole blood; FIG. 4C shows results with 45% v/v heparin-treated whole blood.

FIG. 5A, FIG. 5B, FIG. 5C, FIG. 5D, FIG. 5E, and FIG. 5F are a set of photographs showing amplification of the 322-bp fragment of the human IGF gene in PCR reactions containing 5-30% v/v heparin-treated whole blood by six Taq mutants. FIG. 5A shows results with Taq-1C2; FIG. 5B shows results with Taq-42; FIG. 5C shows results with Taq-5A2; FIG. 5D shows results with Taq-2C2; FIG. 5E shows results with Taq-5; FIG. 5F shows results with Taq-7P.

DETAILED DESCRIPTION OF THE INVENTION

Figure 2:
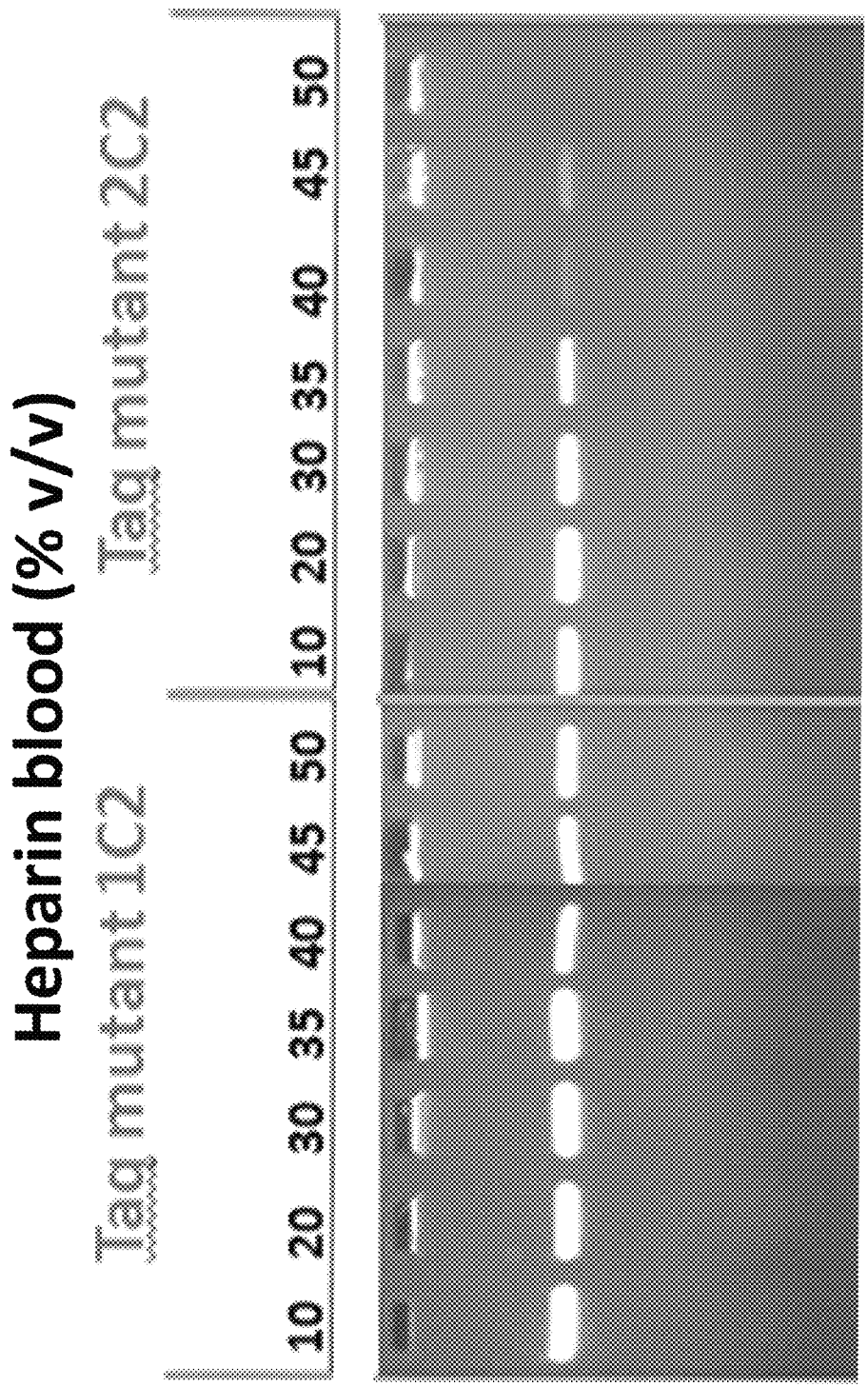
FIG. 2 is a photograph showing amplification by Taq mutants 1C2 and 2C2 of a 322-bp fragment of the human IGF gene from DNA in PCR reactions containing 10-50% v/v heparin-treated whole blood.

This invention is based, at least in part, on the unexpected discovery of certain mutant DNA polymerases that are more resistant to inhibitors present in blood samples than their wild-type counterparts.

1. Mutant DNA Polymerases

In a first aspect, the present invention provides genetically engineered or mutant, isolated DNA polymerases, which can be suitable for use in PCR reactions.

As disclosed herein, the engineered DNA polymerases of the invention are resistant to one or more inhibitors of a particular DNA polymerase. More specifically, a DNA polymerase according to this aspect of the present invention comprises at least one mutation, as compared to the wild-type DNA polymerase from which it derives, that allows for acceptable levels of DNA polymerization or correct amplification of a desired product during PCR in the presence of one or more inhibitors that reduce the polymerization rate of the wild-type DNA polymerase to a level that does not permit successful product formation in a PCR reaction. Any assay known in the art for determining polymerase activity and/or product formation can be used, for example, an assay as described in the examples below.

The DNA polymerases of this aspect of the invention typically have (i) a first mutation at residue 507 of SEQ ID NO: 4 (a wild-type *Thermus aquaticus* Taq DNA polymerase) or at a residue corresponding to residue 507 of the wild-type Taq DNA polymerase in another thermostable Type-A DNA polymerase; and (ii) additional mutations at residues 59, 155, 245, and 749 of the wild-type Taq DNA polymerase, or at corresponding residues in the another thermostable Type-A DNA polymerase. FIG. 1 lists ten examples of such a wild-type DNA polymerase and an alignment of their primary amino acid sequences. Residues corresponding to 59, 155, 245, 507, and 749 of SEQ ID NO:

4 in each polymerase can be located in FIG. 1. In exemplary embodiments, the following mutations are present in the Taq DNA polymerase, or at residues corresponding to these residues at G59W, V155I, L245M, E507K, and F749I of SEQ ID NO: 4. Shown below are the amino acid sequence of one exemplary mutant, Taq 1C2, where the five mutations are underlined, and its coding sequence (SEQ ID NOs 11 and 12, respectively):

SEQ ID NO: 11

MRGMLPLFEPKGRVLLVDGHHLAYRTFHALKGLTTSRGEPVQAVYGFAKSLLKALKED<u>W</u>DAVIV

VFDAKAPSFRHEAYGGYKAGRAPTPEDFPRQLALIKELVDLLGLARLEVPGYEADDVLASLAKK

AEKEGYEVRILTADKDLYQLLSDRIH<u>I</u>LHPEGYLITPAWLWEKYGLRPDQWADYRALTGDESDN

LPGVKGIGEKTARKLLEEWGSLEALLKNLDRLKPAIREKILAHMDDLKLSWD<u>M</u>AKVRTDLPLEV

DFAKRREPDRERLRAFLERLEFGSLLHEFGLLESPKALEEAPWPPPEGAFVGFVLSRKEPMWAD

LLALAAARGGRVHRAPEPYKALRDLKEARGLLAKDLSVLALREGLGLPPGDDPMLLAYLLDPSN

TTPEGVARRYGGEWTEEAGERAALSERLFANLWGRLEGEERLLWLYREVERPLSAVLAHMEATG

VRLDVAYLRALSLEVAEEIARLEAEVFRLAGHPFNLNSRDQLERVLFDELGLPAIGKT<u>K</u>KTGKR

STSAAVLEALREAHPIVEKILQYRELTKLKSTYIDPLPDLIHPRTGRLHTRFNQTATATGRLSS

SDPNLQNIPVRTPLGQRIRRAFIAEEGWLLVALDYSQIELRVLAHLSGDENLIRVFQEGRDIHT

ETASWMFGVPREAVDPLMRRAAKTINFGVLYGMSAHRLSQELAIPYEEAQAFIERYFQSFPKVR

AWIEKTLEEGRRRGYVETLFGRRRYVPDLEARVKSVREAAERMA<u>I</u>NMPVQGTAADLMKLAMVKL

FPRLEEMGARMLLQVHDELVLEAPKERAEAVARLAKEVMEGVYPLAVPLEVEVGIGEDWLSAKE

SEQ ID NO: 12

ATGCGTGGCATGCTTCCTCTTTTTGAGCCCAAGGGCCGGGTCCTCCTGGTGGACGGCCACCACCTGGCCTACCGCACCTT

CCACGCCCTGAAGGGCCTCACCACCAGCCGGGGGAGCCGGTGCAGGCGGTCTACGGCTTCGCCAAGAGCCTCCTCAAGG

CCCTCAAGGAGGACTGGGACGCGGTGATCGTGGTCTTTGACGCCAAGGCCCCCTCCTTCCGCCACGAGGCCTACGGGGGG

TACAAGGCGGGCCGGGCCCCCACGCCGGAGGACTTTCCCCGGCAACTCGCCCTCATCAAGGAGCTGGTGGACCTCCTGGG

GCTGGCGCGCCTCGAGGTCCCGGGCTACGAGGCGGACGACGTCCTGGCCAGCCTGGCCAAGAAGGCGGAAAAGGAGGGCT

ACGAGGTCCGCATCCTCACCGCCGACAAAGACCTTTACCAGCTCCTTTCCGACCGCATCCACATCCTCCACCCCGAGGGG

TACCTCATCACCCCGGCCTGGCTTTGGGAAAAGTACGGCCTGAGGCCCGACCAGTGGGCCGACTACCGGGCCCTGACCGG

GGACGAGTCCGACAACCTTCCCGGGGTCAAGGGCATCGGGGAGAAGACGGCGAGGAAGCTTCTGGAGGAGTGGGGGAGCC

TGGAAGCCCTCCTCAAGAACCTGGACCGGCTGAAGCCCGCCATCCGGGAGAAGATCCTGGCCCACATGGACGATCTGAAG

CTCTCCTGGGACATGGCCAAGGTGCGCACCGACCTGCCCCTGGAGGTGGACTTCGCCAAAAGGCGGGAGCCCGACCGGGA

GAGGCTTAGGGCCTTTCTGGAGAGGCTTGAGTTTGGCAGCCTCCTCCACGAGTTCGGCCTTCTGGAAAGCCCCAAGGCCC

TGGAGGAGGCCCCCTGGCCCCCGCCGAAGGGGCCTTCGTGGGCTTTGTGCTTTCCCGCAAGGAGCCCATGTGGGCCGAT

CTTCTGGCCCTGGCCGCCGCCAGGGGGGCCGGGTCCACCGGGCCCCCGAGCCTTATAAAGCCCTCAGGGACCTGAAGGA

GGCGCGGGGCTTCTCGCCAAAGACCTGAGCGTTCTGGCCCTGAGGGAAGGCCTTGGCCTCCCGCCCGGCGACGACCCCA

TGCTCCTCGCCTACCTCCTGGACCCTTCCAACACCACCCCCGAGGGGGTGGCCCGGCGCTACGGCGGGGAGTGGACGGAG

GAGGCGGGGAGCGGGCCGCCCTTTCCGAGAGGCTCTTCGCCAACCTGTGGGGAGGCTTGAGGGGGAGGAGAGGCTCCT

TTGGCTTTACCGGGAGGTGGAGAGGCCCCTTTCCGCTGTCCTGGCCCACATGGAGGCCACGGGGTGCGCCTGGACGTGG

CCTATCTCAGGGCCTTGTCCCTGGAGGTGGCCGAGGAGATCGCCCGCCTCGAGGCCGAGGTCTTCCGCCTGGCCGGCCAC

CCCTTCAACCTCAACTCCCGGGACCAGCTGGAAAGGGTCCTCTTTGACGAGCTAGGGCTTCCCGCCATCGGCAAGACGAA

GAAGACCGGCAAGCGCTCCACCAGCGCCGCCGTCCTGGAGGCCCTCCGCGAGGCCCACCCCATCGTGGAGAAGATCCTGC

AGTACCGGGAGCTCACCAAGCTGAAGAGCACCTACATTGACCCCTTGCCGGACCTCATCCACCCCAGGACGGGCCGCCTC

CACACCCGCTTCAACCAGACGGCCACGGCCACGGGCAGGCTAAGTAGCTCCGATCCCAACCTCCAGAACATCCCCGTCCG

CACCCCGCTTGGGCAGAGGATCCGCCGGGCCTTCATCGCCGAGGAGGGGTGGCTATTGGTGGCCCTGGACTATAGCCAGA

TAGAGCTCAGGGTGCTGGCCCACCTCTCCGGCGACGAGAACCTGATCCGGGTCTTCCAGGAGGGGCGGGACATCCACACG

-continued

```
GAGACCGCCAGCTGGATGTTCGGCGTCCCCGGGAGGCCGTGGACCCCTGATGCGCCGGGCGGCCAAGACCATCAACTT

CGGGGTCCTCTACGGCATGTCGGCCCACCGCCTCTCCCAGGAGCTAGCCATCCCTTACGAGGAGGCCCAGGCCTTCATTG

AGCGCTACTTTCAGAGCTTCCCCAAGGTGCGGGCCTGGATTGAGAAGACCCTGGAGGAGGGCAGGAGGCGGGGGTACGTG

GAGACCCTCTTCGGCCGCCGCCGCTACGTGCCAGACCTAGAGGCCCGGGTGAAGAGCGTGCGGGAGGCGGCCGAGCGCAT

GGCCATCAACATGCCCGTCCAGGGCACCGCCGCCGACCTCATGAAGCTGGCTATGGTGAAGCTCTTCCCCAGGCTGGAGG

AAATGGGGGCCAGGATGCTCCTTCAGGTCCACGACGAGCTGGTCCTCGAGGCCCCAAAAGAGAGGGCGGAGGCCGTGGCC

CGGCTGGCCAAGGAGGTCATGGAGGGGGTGTATCCCCTGGCCGTGCCCCTGGAGGTGGAGGTGGGGATAGGGGAGGACTG

GCTCTCCGCCAAGGAGTAA
```

The DNA polymerases of this aspect of the invention are more resistant to blood treated with heparin or EDTA than their wild-type counterparts. The DNA polymerases can also be more resistant to other inhibitors of Taq DNA polymerase. Examples of these other inhibitors include whole blood (with or without anticoagulants), fractions of whole blood (such as those collected using Guthrie card spots), or components of blood, such as blood plasma, hemoglobin, heme, immunoglobulin G, and lactoferrin; cell lysates, such as ones containing inhibitory concentrations of polysaccharides; plant substances, such as pectin, xylan, and acidic polysaccharides; substances found in soil samples, such as humic acid, fulvic acid, and metal ions, including heavy metals and heavy metal ions; and certain organic solvents. Additional non-limiting examples of the inhibitors include urea, organic and phenolic compounds (e.g., phenol), glycogen, fats, calcium, cellulose, nitrocellulose, mineral oil, pollen, glove powder, SDS, and detergents. Various other inhibitors are known in the art, including without limitation those discussed in Kermekchiev, et al., "Mutants of Taq DNA polymerase resistant to PCR inhibitors allow DNA amplification from whole blood and crude soil samples", Nucleic Acids Research, Vol. 1, p. 14, 2008; and Abu Al-Soud, W., et al., "Capacity of Nine Thermostable DNA Polymerases To Mediate DNA Amplification in the Presence of PCR-Inhibiting Samples", Applied and Environmental Microbiology, Vol. 64, No. 10, October 1998. As the analysis of blood samples from a subject is of importance in medical and forensic analyses, resistance to inhibitors found in blood or blood fractions, including inhibitors that are commonly added to blood to stabilize it and prevent coagulation (e.g., EDTA and/or heparin) is a characteristic of the mutant enzymes according to this invention.

In preferred embodiments, an engineered DNA polymerase according to the invention possesses both increased resistance to at least one DNA polymerase inhibitor mentioned above (e.g., EDTA and/or heparin) and increased DNA polymerization rate as compared to their wild-type counterparts. Such polymerases thus are capable of polymerizing a nucleic acid strand from a primed DNA template at an increased rate even in the presence of substances that are widely known to be inhibitory to the polymerization rate of the wild-type DNA polymerase.

As used herein, the term "genetically engineered" is used interchangeably with "mutant" to indicate a protein or nucleic acid that has been altered in its sequence from the wild-type sequence to include an amino acid residue or nucleotide that is different from the corresponding residue or nucleotide in the wild-type protein or nucleic acid, respectively, from which it is derived. Mutants according to the invention thus include site-directed mutants in which specific residues have been intentionally changed, including deletions of one or more residues; insertions of one or more residues, and replacement of one or more residues of one Type-A DNA polymerase with an exogenous sequence, such as a corresponding sequence of another Type-A DNA polymerase. In situations where a replacement/substitution of one or very few residues is made to create a mutant, it is a straightforward matter to identify the DNA polymerase "from which the mutant is derived." However, in situations where regions of sequences are replaced by other regions of sequences, it is sufficient to understand that the mutant can be considered "derived" from either/any of the wild-type thermostable Type-A DNA polymerases from which sequences of the mutant show identity, particularly any one of the exemplary wild-type DNA polymerases shown below in FIG. 1 (SEQ ID NOs: 1-10).

In the exemplary embodiments discussed in detail herein, the DNA polymerases of the invention are mutant forms of wild-type Taq DNA polymerase, which have altered features that provide the mutant polymerases with advantageous properties. However, it is to be understood that the invention is not limited to the exemplary embodiments discussed in detail below. For example, the invention includes mutants of polymerases other than Taq DNA polymerase, such as mutants of any thermostable Type-A family DNA polymerase. These mutants can be mutants of the polymerases, including but not limited to those, from species of Thermus or Thermatoga. It is well documented and well understood by those of skill in the art that thermostable Type-A DNA polymerases show high levels of sequence identity and conservation. Thus, it is a simple matter for one of skill in the art to identify residues of one particular Type-A DNA polymerase that correspond to residues of another. Thus, reference herein to specific mutations in wild-type Taq DNA polymerase can easily be correlated to corresponding mutations in other polymerases.

FIG. 1 presents an alignment of the primary amino acid sequences of several non-limiting exemplary thermostable Type-A DNA polymerases. As shown in FIG. 1, various regions of thermostable Type-A DNA polymerases are highly conserved while other regions are variable. Those of skill in the art will immediately recognize and understand that mutations in addition to those specifically identified and discussed herein may be made in the variable regions of Type-A DNA polymerases without altering, or without substantially altering, the polymerase activity of the mutated enzyme. Likewise, conservative mutations at conserved residues may be made without altering, or substantially altering, the polymerase activity of the mutated enzyme. Mutating enzymes based on comparative structure analysis with other related enzymes is a common and useful technique in the molecular biology field that allows a person of skill to reasonably predict the effect of a given mutation on the enzymatic activity of the enzyme. Using the structural data and known physical properties of amino acids, those of skill in the art can mutate enzymes, such as the DNA polymerases encompassed by the present invention, without altering, or without substantially altering, the essential enzymatic characteristics of the enzymes.

As used herein, the term "isolated polypeptide" refers to a polypeptide that has been separated from other proteins, lipids, and nucleic acids with which it is naturally associated. The polypeptide can constitute at least 10% (i.e., any percentage between 10% and 100% inclusive, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide of the invention can be produced by recombinant DNA techniques, or by chemical methods.

The "percent identity" of two amino acid sequences or of two nucleic acids is determined using the algorithm of Karlin and Altschul *Proc. Natl. Acad. Sci. USA* 87:2264-68, 1990, modified as in Karlin and Altschul *Proc. Natl. Acad. Sci. USA* 90:5873-77, 1993. Such an algorithm is incorporated into the NBLAST and XBLAST programs (version 2.0) of Altschul, et al. *J. Mol. Biol.* 215:403-10, 1990. BLAST nucleotide searches can be performed with the NBLAST program, score=100, wordlength-12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

The amino acid composition of the above-mentioned DNA polymerase peptide/polypeptide/protein may vary without disrupting the ability to catalyze the replication of DNA under primer extension reaction conditions and/or PCR reaction conditions as described herein in the presence of EDTA- or heparin-treated blood. For example, it can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Thus, a predicted nonessential amino acid residue in the above-mentioned sequences, such as SEQ ID NO: 11, is preferably replaced with another amino acid residue from the same side chain family. Alternatively, mutations can be introduced randomly along all or part of the sequences, such as by saturation mutagenesis, and the resultant mutants can be screened for the ability to catalyze the replication of DNA under PCR conditions described herein to identify mutants that retain the activity as descried below in, e.g., US 20110027833.

While a variety of mutations can be made at each residue of the above-mentioned wild-type *Thermus aquaticus* Taq DNA polymerase (SEQ ID NO: 4) or corresponding residue of other wild-type DNA polymerase (e.g., SEQ ID NOs: 1-3 and 5-10) noted above, mention may be made of the following non-limiting mutations regarding the mutants disclosed herein, which have mutations at G59, V155, L245, E507, and F749 of SEQ ID NO: 4. In some embodiments, each residue at these positions is altered to another member of the respective families based on side chain similarity.

As those of skill in the art will immediately recognize, equivalent sequences of those of the exemplary SEQ ID NOs can be easily created by making one or more conservative substitutions at one or more residues not specified. Such equivalent sequences retain the essential polymerase characteristics of the mutant enzymes. The various conservative substitutions for different amino acids are discussed above and known in the art. Important regions and residues for DNA polymerase activity of Taq DNA polymerase and other Type-A DNA polymerases are well characterized, and those of skill in the art are well aware of which regions and residues can be altered without disrupting the activity of the DNA polymerase of interest. See, e.g., Albà, Replicative DNA polymerases, Genome Biol. 2001; 2(1): reviews3002.1-reviews3002.4 and Steitz, DNA Polymerases: Structural Diversity and Common Mechanisms, Jun. 18, 1999 The Journal of Biological Chemistry, 274, 17395-17398.

An exemplary comparison of selected thermostable Type-A polymerases is provided in FIG. 1 to give the reader an understanding of conserved and variable regions within this group of enzymes; however, those of skill in the art will be aware of other alterations that can be made without substantially altering the activities discussed herein. In view of the fact that production of recombinant proteins is a routine matter in the field of biotechnology today, and as polymerase assays, such as Taq DNA polymerase assays, are well known and widely practiced as routine assays, production of mutant polymerases according to the present invention using the information provided herein is a routine matter for those of skill in the art. Automation and very powerful techniques and kits allow those practicing the invention to rapidly and routinely identify mutants according to the invention, and identify the particular levels of polymerase activity of interest (i.e., polymerization rate and polymerization rate in the presence of inhibitor(s)).

The invention also provides a functional equivalent of a peptide, polypeptide, or protein of this invention, which refers to a polypeptide derivative of the peptide, polypeptide, or protein, e.g., a protein having one or more point mutations, insertions, deletions, truncations, a fusion protein, or a combination thereof. It retains substantially the activity of the above-mentioned DNA polymerase under PCR conditions described herein (e.g., a PCR reaction mixture containing a blood sample that has been pre-treated with EDTA and/or heparin and accounts for at least 1% (e.g., 2%, 2.5%, 5%, 10%, 20%, 25%, 30%, 35%, 40%, 45%, or 50%) v/v of the mixture.). The isolated polypeptide can contain SEQ ID NO: 11 or a functional fragment or equivalent thereof. In general, the functional equivalent is at least 70% (e.g., any number between 70% and 100%, inclusive, e.g., 70%, 75%, 80%, 85%, 90%, 95%, and 99%) identical to SEQ ID NO: 11.

A polypeptide described in this invention can be obtained as a recombinant polypeptide. To prepare a recombinant polypeptide, a nucleic acid encoding it can be linked to another nucleic acid encoding a fusion partner, e.g., glutathione-s-transferase (GST), 6x-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention. Alternatively, the peptides/polypeptides/proteins of the invention can be chemically synthesized (see e.g., Creighton, "Proteins: Structures and Molecular Principles," W.H. Freeman & Co., NY, 1983), or produced by recombinant DNA technology as described herein. For additional guidance, skilled artisans may consult Frederick M. Ausubel et al., Current Protocols in Molecular Biology, John Wiley & Sons, 2003; and Sambrook et al., Molecular Cloning, A Laboratory Manual," Cold Spring Harbor Press, Cold Spring Harbor, N.Y., 2001).

The mutant DNA polymerases of the present invention can be provided in purified or isolated form, or can be part of a composition. Preferably, where in a composition, the mutant DNA polymerases are first purified to some extent, more preferably to a high level of purity (e.g., about 80%, 90%, 95%, or 99% or higher). Compositions according to the invention can be any type of composition desired, but typically are aqueous compositions suitable for use as, or inclusion in, a composition for amplification of a target nucleic acid, and in particular for blood-based amplification, such as through use of a PCR technique. As such, the compositions typically comprise at least one substance other than the mutant DNA polymerase, such as water, glycerol or another stabilizing agent, an aqueous buffer, an aqueous salt buffer, a divalent metal (e.g., magnesium) and the like. In exemplary embodiments, the compositions comprise some or all of the solvents, salts, buffers, nucleotides, and other reagents typically present in a PCR reaction. Thus, in some embodiments, the compositions comprise a magnesium salt (e.g., magnesium chloride or magnesium sulfate), one or more nucleoside triphosphates, one or more nucleic acid primers or probes, one or more additional nucleic acid polymerases or fragments thereof having desired activities, one or more polymerization detection agents (e.g., specific or non-specific dyes or fluorescent molecules), and/or one or more nucleic acid templates for amplification or sequencing. Other exemplary substances include detergents, DMSO, DMF, gelatin, glycerol, betaine, spermidine, T4 gene 32 protein, E. coli SSB, BSA, and ammonium sulfate. Those of skill in the art are well aware of the various substances that can be included in polymerization reaction compositions, and as such an exhaustive list is not necessary here.

2. Nucleic Acids, Vectors, and Host Cells

The present invention also provides a nucleic acid that encodes any of the mutant DNA polymerase polypeptides mentioned above. Preferably, the nucleic acid is isolated and/or purified. A nucleic acid refers to a DNA molecule (for example, but not limited to, a cDNA or genomic DNA), an RNA molecule (for example, but not limited to, an mRNA), or a DNA or RNA analog. A DNA or RNA analog can be synthesized from nucleotide analogs. The nucleic acid molecule can be single-stranded or double-stranded. An "isolated nucleic acid" is a nucleic acid, the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

The present invention also provides recombinant constructs or vectors having one or more of the nucleotide sequences described herein. Examples of the constructs include a vector, such as a plasmid or viral vector, into which a nucleic acid sequence of the invention has been inserted, in a forward or reverse orientation. In a preferred embodiment, the construct further includes regulatory sequences, including a promoter, operably linked to the sequence. Large numbers of suitable vectors and promoters are known to those of skill in the art, and are commercially available. Appropriate cloning and expression vectors for use with prokaryotic and eukaryotic hosts are also described in Sambrook et al. (2001, Molecular Cloning: A Laboratory Manual, Cold Spring Harbor Press).

A vector refers to a nucleic acid molecule capable of transporting another nucleic acid to which it has been linked. The vector can be capable of autonomous replication or integration into a host DNA. Examples of the vector include a plasmid, cosmid, or viral vector. The vector of this invention includes a nucleic acid in a form suitable for expression of the nucleic acid in a host cell. Preferably the vector includes one or more regulatory sequences operatively linked to the nucleic acid sequence to be expressed. A "regulatory sequence" includes promoters, enhancers, and other expression control elements (e.g., polyadenylation signals). Regulatory sequences include those that direct constitutive expression of a nucleotide sequence, as well as inducible regulatory sequences. The design of the expression vector can depend on such factors as the choice of the host cell to be transformed, transfected, or infected the level of expression of protein desired, and the like.

Examples of expression vectors include chromosomal, nonchromosomal and synthetic DNA sequences, e.g., derivatives of or Simian virus 40 (SV40), bacterial plasmids, phage DNA, baculovirus, yeast plasmids, vectors derived from combinations of plasmids and phage DNA, viral DNA such as vaccinia, adenovirus, fowl pox virus, and pseudorabies. However, any other vector may be used as long as it is replicable and viable in the host. The appropriate nucleic acid sequence may be inserted into the vector by a variety of procedures. In general, a nucleic acid sequence encoding one of the polypeptides described above can be inserted into an appropriate restriction endonuclease site(s) by procedures known in the art. Such procedures and related sub-cloning procedures are within the scope of those skilled in the art.

The expression vector can also contain a ribosome binding site for translation initiation, and a transcription terminator. The vector may include appropriate sequences for amplifying expression. In addition, the expression vector preferably contains one or more selectable marker genes to provide a phenotypic trait for selection of transformed host cells such as dihydrofolate reductase or neomycin resistance for eukaryotic cell cultures, or such as tetracycline or ampicillin resistance in E. coli.

The vector containing the appropriate nucleic acid sequences as described above, as well as an appropriate promoter or control sequence, can be employed to transform, transfect, or infect an appropriate host to permit the host to express the polypeptides described above (e.g., SEQ ID NO: 11). Examples of suitable expression hosts include bacterial cells (e.g., *E. coli, Streptomyces, Salmonella typhimurium*), fungal cells (yeast), insect cells (e.g., *Drosophila* and *Spodoptera frugiperda* (Sf9)), animal cells (e.g., CHO, COS, and HEK 293), adenoviruses, and plant cells. The selection of an appropriate host is within the scope of those skilled in the art. In some embodiments, the present invention provides methods for producing the above mentioned polymerase polypeptides by transforming, transfecting, or infecting a host cell with an expression vector having a nucleotide sequence that encodes one of the polypeptides. The host cells are then cultured under a suitable condition, which allows for the expression of the polypeptide.

3. Methods and Uses

The mutant DNA polymerases of the invention are suitable for various uses, including primer extension, nucleic acid polymerization reactions, and others requiring DNA polymerases.

For example, the engineered mutant DNA polymerases can be used in methods of primer extension or polymerizing nucleic acids from a primer or set of primers and a nucleic acid template. In general, the methods comprise: (A) exposing (such as combining together, mixing, contacting etc.) an engineered DNA polymerase according to the invention to (1) a target nucleic acid and (2) at least one primer suitable for priming polymerization of a nucleic acid that is complementary to one strand of the target nucleic acid, and (B) exposing (such as subjecting) the polymerase, target nucleic acid, and primer(s) to conditions that allow polymerization of nucleic acids from the primer(s). The step of exposing the polymerase to the other substances can be any action that results in exposure of the recited substances to each other such that they can physically interact. It thus can comprise adding the substances together in a composition, mixing the substances together in a composition (i.e., a mixture), etc. Exposing may be performed fully or partially manually, or fully or partially automatically (i.e., by way of machinery, robotics, etc.). As those of skill in the art are aware, a wide variety of nucleic acids can be subjected to copying, amplifying, sequencing, etc. Thus, the invention is not limited by the target nucleic acid, its sequence, length, etc. Further, those of skill in the art are fully aware of the parameters to be considered when designing primers for priming polymerization of a nucleic acid based on a target nucleic acid template. Thus, the invention is not limited by the identity or sequence of the primers. It is to be understood that, where amplification is desired (e.g., PCR), two primers having different sequences and having specificity for two different sequences on opposite strands of the target nucleic acid should be used. In addition, the step of exposing the combined substances to conditions that allow for polymerization can be any action that allows for polymerization. Many conditions suitable for polymerization are known in the art, and those of skill in the art may select any appropriate conditions, as the situation requires, without undue or excessive experimentation. Parameters to be considered include, but are not necessarily limited to, salt concentration, metal ion or chelator concentration, buffer concentration and identity, presence or absence of detergents and organic solvents, concentration of polymerase or other enzymes, presence or concentration of nucleotides or modified nucleotides, presence or concentration of polymerization inhibitors or terminators, presence or concentration of probes or dyes for detection of polymerization products, temperature, and length of time of exposure. In exemplary embodiments, the conditions that allow polymerization of nucleic acids from the primer(s) are conditions for a PCR reaction. As will be recognized by those of skill in the art, the step of exposing the substances to conditions for polymerization can be considered as a step of polymerizing, such as a step of amplifying a nucleic acid template.

The polymerases are advantageously used in any variation or type of PCR reaction for amplification of nucleic acids, including both DNA and RNA amplifications. For amplification of RNA templates (e.g., mRNAs or microRNAs), an RNA-dependent DNA polymerase (e.g., a reverse transcriptase; RT) can be used to make a DNA strand complementary to the RNA template, and a DNA polymerase of the invention can be used to amplify the DNA complementary strand.

In some exemplary embodiments, the PCR method is conducted on "dirty" samples, such as blood. In general, as used herein, a "dirty" sample is one that includes undefined substances, typically present originally in the environment where the target nucleic acid was present. Thus, a dirty sample in general is a sample in which the target nucleic acid was not purified prior to inclusion in the polymerization reaction.

Accordingly, the polymerase mutants and related methods can be used in various ways. For examples, they can be used for detecting blood infections at an early stage of infection with a pathogen and more particularly for detecting pathogens at low concentrations in circulation from a volume of blood from a subject (e.g., a patient) or in a biological product. Examples of such pathogens include fungi, bacteria (e.g., *Mycobacterium tuberculosis* and *H. pylori*) and viruses (e.g., HIV, HBV, and HCV). They also can be used for detecting genetic mutations, markers or polymorphisms (e.g., Single Nucleotide Polymorphism) associated with cancer or genetic disorders. Furthermore, they can be used for analysis of rare cells, such as foetal cells in a maternal blood sample or micrometastatic tumor cells, the detection of which is often complicated by the low abundance of such cells and because the biological sample often will comprise a majority of other cells or tissue material besides the rare cell of interest. The ability to analyze rare cells and other biological material of limited availability allows the development of new diagnostic methods with a less invasive character. See, e.g., US Applications 20130316925, 20130157253, 20120329061, 20120070827, 20120034614, 20070281307, 20070105121, 20050009108, and 20020155519. All of these references are incorporated by reference herein in their entireties.

Due to their increased polymerization rate, the polymerase enzymes of the present invention are also well suited for "fast PCR" reactions, such as those described in, e.g., US20110027833, the content of which is incorporated by reference. Further, due to their resistance to inhibitors found in blood and blood products, they are particularly well suited for "fast PCR" reactions in samples that contain blood or fractions of blood. Preferably, they are well suited for "fast PCR" reactions in "dirty" samples, such as those containing blood or fractions of blood that have been treated with anticoagulants such as EDTA and heparin.

In some embodiments, two or more primers having different sequences are used in the method. For example, in some embodiments two primers are used, where one primer specifically binds to one strand of the template DNA and the other binds to the other strand of the template DNA, allowing for production of a double-stranded polymerization product. In some embodiments, one primer is specific for a sequence present on a single-stranded RNA template, such as an mRNA. Polymerization of a first complementary strand of the RNA from the first primer provides a template for the second primer. Subsequent to a first polymerization, the first primer can prime polymerization from either the template RNA or the DNA complement. One or more nucleic acid probes having sequence specificity for the target nucleic acid (including a complementary strand of the target, where the target is single-stranded) can be included in the method to provide a means for detection.

Many PCR methods include probes, dyes, or other substances that allow for detection of polymerization (e.g., amplification) products. One example of such methods is Real-Time PCR. Accordingly, the method can include a step of including in the polymerization reaction a substance that allows for detection of polymerization products. Furthermore, the method of the invention encompasses methods that include one or more control reactions to determine if the methods, or particular method steps, have been performed successfully. The control reactions can be positive control reactions or negative control reactions. Those of skill in the art are fully capable of devising appropriate control reaction conditions without the need for particular steps to be detailed herein.

4. Kits

The invention encompasses kits and diagnostic systems for nucleic acid copying, primer extension, or amplification for detecting a target sequence. To that end, one or more of the reaction components for the methods disclosed herein can be supplied in the form of a kit for use in the detection of a target nucleic acid. In such a kit, an appropriate amount of one or more reaction components is provided in one or more containers or held on a substrate (e.g., by electrostatic interactions or covalent bonding).

The kit described herein includes one or more of the mutant DNA polymerases described above. The kit can include one or more containers containing one or more mutant DNA polymerases of the invention. A kit can contain a single mutant polymerase in a single container, multiple containers containing the same mutant DNA polymerase, a single container containing two or more different mutant DNA polymerases of the invention, or multiple containers containing different mutant DNA polymerases or containing mixtures of two or more mutant DNA polymerases. Any combination or permutation of DNA polymerase(s) and containers is encompassed by the kits of the invention. In a preferred embodiment, the kit includes 1) 3 separate tubes containing a polymerase, a buffer (with $Mg^{2+}$), and nucleotides or 2) a master mix containing a mixture of polymerase, buffer components, $Mg^{2+}$, and nucleotides. Users of the kit can add suitable nucleic acid templates or test samples containing such templates (e.g., blood) and primers depending on their purposes and assay designs. The polymerase and/or buffer (or master mix) can further contain one or more detergents, and may also contain hot start antibody. Master mixes for real time PCR could additionally contain dye.

The kit may also contain additional materials for practicing the above-described methods. In some embodiments, the kit contains some or all of the reagents, materials for performing a method that uses a mutant DNA polymerase according to the invention. The kit thus may comprise some or all of the reagents for performing a PCR reaction using the DNA polymerase of the invention. Some or all of the components of the kits can be provided in containers separate from the container(s) containing the polymerases of the invention. Examples of additional components of the kits include, but are not limited to, one or more different polymerases, one or more primers that are specific for a control nucleic acid or for a target nucleic acid, one or more probes that are specific for a control nucleic acid or for a target nucleic acid, buffers for polymerization reactions (in 1× or concentrated forms), magnesium, nucleotides and one or more dyes or one or more fluorescent molecules for detecting polymerization products. The kit may also include one or more of the following components: supports, terminating, modifying or digestion reagents, osmolytes, and an apparatus for detecting a detection probe.

The reaction components used in an amplification and/or detection process may be provided in a variety of forms. For example, the components (e.g., enzymes, nucleotide triphosphates, probes and/or primers) can be suspended in an aqueous solution or as a freeze-dried or lyophilized powder, pellet, or bead. In the latter case, the components, when reconstituted, form a complete mixture of components for use in an assay.

A kit or system may contain, in an amount sufficient for at least one assay, any combination of the components described herein, and may further include instructions recorded in a tangible form for use of the components. In some applications, one or more reaction components may be provided in pre-measured single use amounts in individual, typically disposable, tubes or equivalent containers. With such an arrangement, the sample to be tested for the presence of a target nucleic acid can be added to the individual tubes and amplification carried out directly. The amount of a component supplied in the kit can be any appropriate amount, and may depend on the target market to which the product is directed. General guidelines for determining appropriate amounts may be found in, for example, Joseph Sambrook and David W. Russell, Molecular Cloning: A Laboratory Manual, 3rd edition, Cold Spring Harbor Laboratory Press, 2001; and Frederick M. Ausubel, Current Protocols in Molecular Biology, John Wiley & Sons, 2003.

The kits of the invention can comprise any number of additional reagents or substances that are useful for practicing a method of the invention. Such substances include, but are not limited to: anticoagulants (e.g., EDTA and heparin), reagents (including buffers) for lysis of cells, divalent cation chelating agents or other agents that inhibit unwanted nucleases, control DNA for use in ensuring that the polymerase and other components of reactions are functioning properly, DNA fragmenting reagents (including buffers), amplification reaction reagents (including buffers), and wash solutions. The kits of the invention can be provided at any temperature. For example, for storage of kits containing protein components or complexes thereof in a liquid, it is preferred that they are provided and maintained below 0° C., preferably at or below −20° C., or otherwise in a frozen state.

The container(s) in which the components are supplied can be any conventional container that is capable of holding the supplied form, for instance, microfuge tubes, ampoules, bottles, or integral testing devices, such as fluidic devices, cartridges, lateral flow, or other similar devices. The kits can include either labeled or unlabeled nucleic acid probes for use in amplification or detection of target nucleic acids. In some embodiments, the kits can further include instructions to use the components in any of the methods described herein, e.g., a method using a crude matrix without nucleic acid extraction and/or purification.

The kits can also include packaging materials for holding the container or combination of containers. Typical packaging materials for such kits and systems include solid matrices (e.g., glass, plastic, paper, foil, micro-particles and the like) that hold the reaction components or detection probes in any of a variety of configurations (e.g., in a vial, microtiter plate well, microarray, and the like).

As used herein, a DNA polymerase that is "resistant to an inhibitor," refers to a DNA polymerase mutant or variant that allows for acceptable levels of DNA polymerization or/and correct amplification of a desired product during PCR in the presence of such an inhibitor that reduces the polymerization rate of the wild-type DNA polymerase to a level that does not permit successful product formation in a PCR reaction. In certain embodiments, the inhibitor is whole blood treated with EDTA or heparin. And, the term "resistant to an inhibitor" also refers to the situations where the DNA polymerase mutant or variant allows for acceptable levels of DNA polymerization or/and correct amplification of a desired product from a PCR reaction mixture containing a blood sample that has been pre-treated with such an inhibitor and accounts for at least 1% (e.g., 2%, 2.5%, 5%, 10%, 20%, 25%, 30%, 35%, 40%, 45%, or 50%) v/v of the mixture.

As used herein, the term "target nucleic acid" or "target" refers to a nucleic acid containing a target nucleic acid sequence. A target nucleic acid may be single-stranded or double-stranded, and often is DNA, RNA, a derivative of DNA or RNA, or a combination thereof. A "target nucleic acid sequence," "target sequence" or "target region" means a specific sequence comprising all or part of the sequence of a single-stranded nucleic acid. A target sequence may be within a nucleic acid template, which may be any form of single-stranded or double-stranded nucleic acid. A template may be a purified or isolated nucleic acid, or may be non-purified or non-isolated.

As used herein the term "amplification" and its variants includes any process for producing multiple copies or complements of at least some portion of a polynucleotide, the polynucleotide typically being referred to as a "template." The template polynucleotide can be single stranded or double stranded. Amplification of a given template can result in the generation of a population of polynucleotide amplification products, collectively referred to as an "amplicon." The polynucleotides of the amplicon can be single stranded or double stranded, or a mixture of both. Typically, the template will include a target sequence, and the resulting amplicon will include polynucleotides having a sequence that is either substantially identical or substantially complementary to the target sequence. In some embodiments, the polynucleotides of a particular amplicon are substantially identical, or substantially complementary, to each other; alternatively, in some embodiments the polynucleotides within a given amplicon can have nucleotide sequences that vary from each other. Amplification can proceed in linear or exponential fashion, and can involve repeated and consecutive replications of a given template to form two or more amplification products. Some typical amplification reactions involve successive and repeated cycles of template-based nucleic acid synthesis, resulting in the formation of a plurality of daughter polynucleotides containing at least some portion of the nucleotide sequence of the template and sharing at least some degree of nucleotide sequence identity (or complementarity) with the template. In some embodiments, each instance of nucleic acid synthesis, which can be referred to as a "cycle" of amplification, includes creating free 3' end (e.g., by nicking one strand of a dsDNA) thereby generating a primer and primer extension steps; optionally, an additional denaturation step can also be included wherein the template is partially or completely denatured. In some embodiments, one round of amplification includes a given number of repetitions of a single cycle of amplification. For example, a round of amplification can include 5, 10, 15, 20, 25, 30, 35, 40, 50, 75, 100 or more repetitions of a particular cycle. In one exemplary embodiment, amplification includes any reaction wherein a particular polynucleotide template is subjected to two consecutive cycles of nucleic acid synthesis. The synthesis can include template-dependent nucleic acid synthesis.

The term "primer" or "primer oligonucleotide" refers to a strand of nucleic acid or an oligonucleotide capable of hybridizing to a template nucleic acid and acting as the initiation point for incorporating extension nucleotides according to the composition of the template nucleic acid for nucleic acid synthesis. "Extension nucleotides" refer to any nucleotide capable of being incorporated into an extension product during amplification, i.e., DNA, RNA, or a derivative if DNA or RNA, which may include a label.

"Hybridization" or "hybridize" or "anneal" refers to the ability of completely or partially complementary nucleic acid strands to come together under specified hybridization conditions (e.g., stringent hybridization conditions) in a parallel or preferably antiparallel orientation to form a stable double-stranded structure or region (sometimes called a "hybrid") in which the two constituent strands are joined by hydrogen bonds. Although hydrogen bonds typically form between adenine and thymine or uracil (A and T or U) or cytosine and guanine (C and G), other base pairs may form (e.g., Adams et al., The Biochemistry of the Nucleic Acids, 11th ed., 1992).

The term "stringent hybridization conditions" or "stringent conditions" means conditions in which a probe or oligomer hybridizes specifically to its intended target nucleic acid sequence and not to another sequence. Stringent conditions may vary depending on well-known factors, e.g., GC content and sequence length, and may be predicted or determined empirically using standard methods well known to one of ordinary skill in molecular biology (e.g., Sambrook, J. et al., 1989, Molecular Cloning, A Laboratory Manual, 2nd ed., Ch. 11, pp. 11.47-11.57, (Cold Spring Harbor Laboratory Press, Cold Spring Harbor, N.Y.)).

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

The term "about" generally refers to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

As used herein, the term "subject" refers to any organism having a genome, preferably, a living animal, e.g., a mammal, which has been the object of diagnosis, treatment, observation or experiment. Examples of a subject can be a human, a livestock animal (beef and dairy cattle, sheep, poultry, swine, etc.), or a companion animal (dogs, cats, horses, etc).

The term "biological sample" refers to a sample obtained from an organism (e.g., patient) or from components (e.g., cells) of an organism. The sample may be of any biological tissue, cell(s) or fluid. The sample may be a "clinical sample" which is a sample derived from a subject, such as a human patient or veterinary subject. Such samples include, but are not limited to, saliva, sputum, blood, blood cells (e.g., white cells), amniotic fluid, plasma, semen, bone marrow, and tissue or fine needle biopsy samples, urine, peritoneal fluid, and pleural fluid, or cells therefrom. Biological samples may also include sections of tissues such as frozen sections taken for histological purposes. A biological sample may also be referred to as a "patient sample." A biological sample may also include a substantially purified or isolated protein, membrane preparation, or cell culture.

As used herein, the term "contacting" and its variants, when used in reference to any set of components, includes any process whereby the components to be contacted are mixed into same mixture (for example, are added into the same compartment or solution), and does not necessarily require actual physical contact between the recited components. The recited components can be contacted in any order or any combination (or subcombination), and can include situations where one or some of the recited components are subsequently removed from the mixture, optionally prior to addition of other recited components. For example, "contacting A with B and C" includes any and all of the following situations: (i) A is mixed with C, then B is added to the mixture; (ii) A and B are mixed into a mixture; B is removed from the mixture, and then C is added to the mixture; and (iii) A is added to a mixture of B and C. "Contacting a template with a reaction mixture" includes any or all of the following situations: (i) the template is contacted with a first component of the reaction mixture to create a mixture; then other components of the reaction mixture are added in any order or combination to the mixture; and (ii) the reaction mixture is fully formed prior to mixture with the template.

The term "mixture" as used herein, refers to a combination of elements, that are interspersed and not in any particular order. A mixture is heterogeneous and not spatially separable into its different constituents. Examples of mixtures of elements include a number of different elements that are dissolved in the same aqueous solution, or a number of different elements attached to a solid support at random or in no particular order in which the different elements are not spatially distinct. In other words, a mixture is not addressable. To be specific, an array of surface-bound oligonucleotides, as is commonly known in the art and described below, is not a mixture of surface-bound oligonucleotides because the species of surface-bound oligonucleotides are spatially distinct and the array is addressable.

EXAMPLE 1

Generation and Screening of Mutant Polymerases

Mutant Taq DNA polymerases were generated by random mutagenesis of a nucleic acid comprising the sequence of SEQ ID NO: 4, which encodes a wild-type *Thermus aquaticus* Taq DNA polymerase in the manner described in US 20110027833, the content of which is incorporated by reference in its entirety.

Briefly, random mutant libraries were subjected to 5 rounds of selection under fast cycling conditions, followed by screening (after rounds 2, 4, and 5) to identify clones that support amplification using shortened extension times. Polymerases showing improved performance during Real-Time PCR under fast cycling conditions, as compared to wild-type Taq DNA polymerase, were subjected to DNA sequencing to identify mutations. Mutations of interest appearing in fast-amplifying clones were identified and recombined using site-directed mutagenesis. Recombinants were screened using Real-Time PCR with fast cycling conditions. Mutant polymerases that outperformed both wild-type Taq and the best performers from the original selection/screening were identified, sequenced, and purified for further characterization to identify clones with combinations of mutations that support PCR using the shortest extension times.

Selected mutant polymerases obtained in the manner described above were further characterized to assess their ability to polymerize a nucleic acid chain from a primer in the presence of blood treated with anticoagulants such as EDTA and heparin.

EXAMPLE 2

Characterization of Mutant Enzymes' Resistance to EDTA

In this example, assays were carried out to examine the ability of various mutant enzymes to amplify a target DNA during End-Point PCR in the presence of whole blood that had been collected and stored in EDTA, which was known to inhibit Taq DNA polymerase activity.

Specifically, PCR reactions containing components typical for End-Point assays were assembled using wild-type Taq (Taq2000, Agilent Technologies; SEQ ID NO: 4) and a number of mutants derived from it. The mutants examined include the above-mentioned mutant Taq 1C2, a number of mutants described in US 20110027833, including Taq 42, Taq 3B, Taq 2C2, and Taq 5A2, and three other mutants Taq 7P, Taq 8P, and Taq 5. The table below summarizes the mutations in these mutants:

| Enzyme | G59W | V155I | L245M | L375V | E507K | E734G | F749I | K508R |
|---|---|---|---|---|---|---|---|---|
| Taq 7B (WT) | − | − | − | − | − | − | − | − |
| Taq 42 | + | − | + | + | + | + | + | + |
| Taq 2C2 | + | + | + | + | + | + | + | − |
| Taq 1C2 | + | + | + | − | + | − | + | − |
| Taq 3B | − | + | + | − | + | − | + | − |
| Taq 1 | + | − | − | − | − | − | − | − |
| Taq 8P | − | + | − | − | − | − | − | − |
| Taq 5A2 | − | − | − | − | + | − | − | − |
| Taq 7P | − | − | − | − | − | − | + | − |
| Taq 5 | + | + | + | − | − | − | − | − |

To examine these enzymes' resistance to EDTA, PCR was performed to amplify a 322 base-pair target of human IGF gene from human genomic DNA in whole blood that had been treated with EDTA. The EDTA-treated blood contains 1.8 µg/µl $K_2$EDTA. In the PCR reactions, final concentrations of the blood ranged from 1% to 65% v/v. The human blood was added individually as the template to enzyme master mixes previously aliquotted into PCR strip tubes. Each polymerase-template combination was assayed in duplicate. Amplification was performed using 50 ng of each enzyme per 50 µl reaction. The thermocycling parameters were as follows: 95° C. for 5 minutes; 95° C. for 30 seconds; 60° C. for 30 seconds, and 72° C. for 1 minute, for 30 cycles.

The amplification products were fractionated on an agarose gel pre-stained with ethidium bromide. The highest amount of blood that produced PCR product is summarized in the table below:

| Enzyme | EDTA-blood |
| --- | --- |
| Taq 7B (WT) | <1% |
| Taq 42 | 60% |
| Taq 3B | 50% |
| Taq 2C2 | 65% |
| Taq 5A2 | 45% |
| Taq 7P | 15% |
| Taq 8P | 15% |
| Taq 1C2 | 60% |
| Taq 1 | 15% |

The results indicate that the wild-type Taq DNA polymerase was able to amplify the 322-bp product only when the EDTA-treated blood is less than 1% v/v of the reaction mixture. In contrast, many of the mutants were capable of producing specific target products in the presence of as high as more than 50% EDTA-treated blood. Among them, Taq 42, Taq 2C2, and Taq 1C2 are most resistant to EDTA, and they were capable of producing specific target products in the presence of 60%, 65%, and 60% EDTA-treated blood samples respectively.

EXAMPLE 3

Characterization of Mutant Enzymes' Resistance to Heparin

Heparin is another routinely used anticoagulant. In this example, assays were carried out to examine the abilities of the Taq 2C2 and Taq 1C2 mutant enzymes to amplify a target DNA in the presence of whole blood that had been treated with heparin. The heparinized blood contains 15.8USP units/ml sodium heparin.

PCR reactions containing components typical for End-Point assays were assembled and the assays carried out in the manner described above except that heparin-treated blood was used as the template for each reaction. In the PCR reactions, final concentrations of the heparin-treated blood ranged from 10% to 50% v/v. The results are shown in FIG. 2. As shown in FIG. 2, Taq 2C2 was able to produce a substantial amount of specific target product in the presence of 10-30% v/v heparin-treated blood. But, the amounts or yields of the target product generally decreased as the amount of heparin-treated blood increased. When the heparin-treated blood was 30% v/v or more, Taq 2C2 showed a rapid loss in activity and a total lack of activity in the presence of 50% v/v of heparin-treated blood. In contrast, Taq 1C2 consistently produced a substantial amount of specific products across the entire ranges tested (10% to 50% v/v). More surprisingly, Taq 1C2 kept almost the same activity level and produced an essentially equivalent amount of product in the presence of 10-50% v/v heparin-treated blood.

These results support that the Taq 1C2 mutant DNA polymerase possesses advantageous properties as compared to other EDTA-resistant mutant DNA polymerases described in Example 2.

Additional assays were further carried out to examine the abilities of the Taq 1C2, 2C2, 42, 5, 5A2, and 7P mutants to amplify the above-mentioned 322 base-pair target of human IGF gene from human genomic DNA in heparin-treated whole blood in the same manner on a SureCycler. The thermocycling parameters were as follows: 95° C. for 5 minutes followed by 30 cycles of 95° C. for 30 seconds, 60° C. for 30 seconds, and 72° C. for 1 minute. The reaction mixtures contained 300 nM each primer, a reaction buffer containing 15 mM Tris pH 8.8, 96 mM KCl, 2% DMSO, 2.5 mM $MgCl_2$, 200 µM for each of dA, dG, dC, and dT, 0.5 µl of the Taq mutant at 50 ng/1 IN FDB with 0.5% each Igepal and Tween-20. After centrifugation to settle debris, 8 µl of each 50 µl reaction mixture was run on Nusieve TBE gels. The results are shown in FIG. 5.

Again, the Taq 1C2 mutant retained almost the same activity level and produced an essentially equivalent amount of product in the presence of 5-30% v/v heparin-treated blood. And, the Taq 1C2 mutant is the only one that amplified the target DNA in the presence of 30% v/v heparin-treated blood.

EXAMPLE 4

Comparison of Taq 1C2 with Commercially Available DNA Polymerases

In this example, the Taq 1C2 mutant DNA polymerase was further compared with a number of commercially available DNA polymerases. To that end, the target amplified from blood was a 232-bp non-coding single copy region of the human genome.

Briefly, whole blood samples were obtained from a subject and treated with either EDTA or heparin according to standard protocols. These samples were used as templates to amplify the 232-bp region. Each PCR reaction was 50 ul volume and cycled 30× using the Agilent SureCycler (Agilent Technologies, Inc.); 400 nM of each primer was used in all cases. The DNA polymerases used include the Taq 1C2 mutant ("Agilent") and polymerases marketed by a number of manufactures, including Kapa Biosystems Blood PCR Mix A ("KAPA-A," Kapa Biosystems), DNA Polymerase Technology Omni KlenTaq ("KlenTaq," Sigma-Aldrich Co. LLC), Clontech Terra Direct ("ClonTech," Clontech Laboratories, Inc.) and Thermo Scientific Phusion Blood Direct ("Thermo," Thermo Scientific). The reaction mixes were assembled according to manufacturers' instructions. Thermal cycling profiles comply with manufacturers' recommendations and are detailed below:

| Agilent, KAPA-A | | KlenTaq | | ClonTech | | Thermo | |
| --- | --- | --- | --- | --- | --- | --- | --- |
| 90° 5' | ×1 | 94° 5' | ×1 | 98° 2' | ×1 | 98° 5' | ×1 |
| ↓ | | ↓ | | ↓ | | ↓ | |
| 94° 30" | | 94° 40" | | 98° 10" | | 98° 1" | |

-continued

| Agilent, KAPA-A | KlenTaq | ClonTech | Thermo |
|---|---|---|---|
| 60° 30" ×30 72° 1' | 60° 40" ×30 68° 30" | 60° 15" ×30 68° 15' | 60° 1" ×30 72° 5' |

Figure 3A:
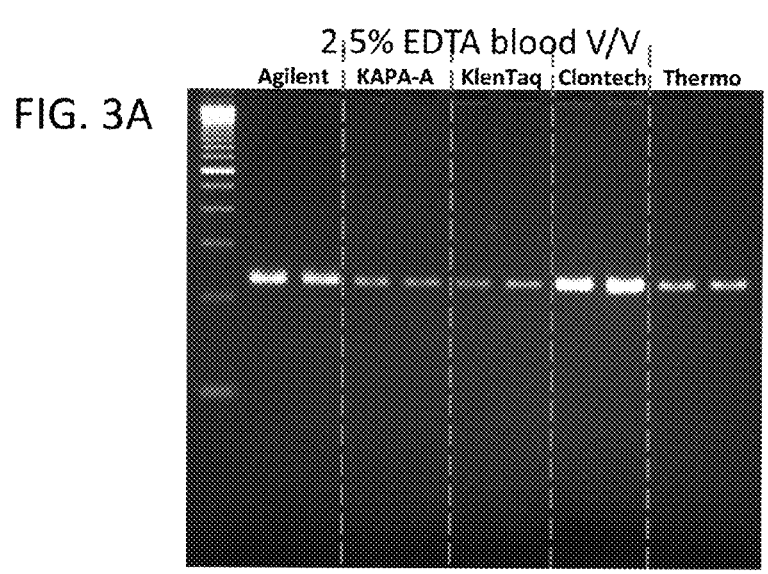
FIG. 3A, FIG. 3B, and FIG. 3C are a set of photographs showing comparison of the activity of Taq mutant 1C2 with those of DNA polymerases from different sources in the presence of EDTA-treated whole blood.
Figure 3B:
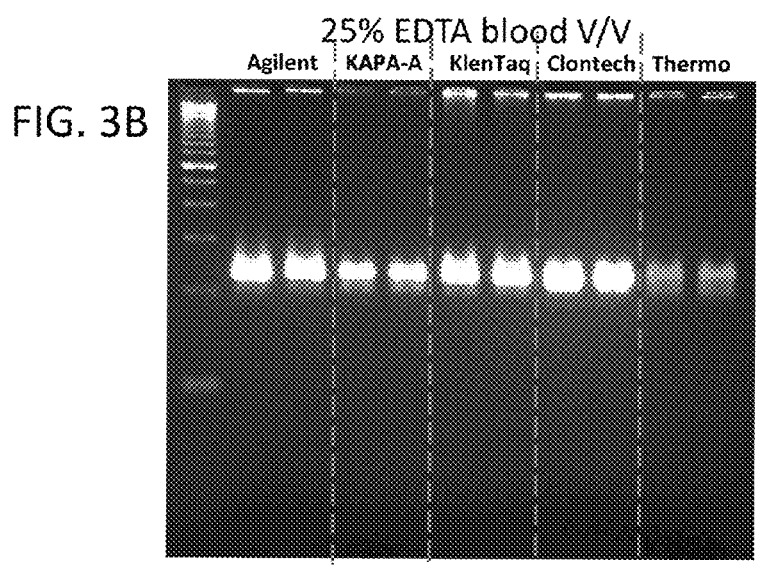
Figure 3C:
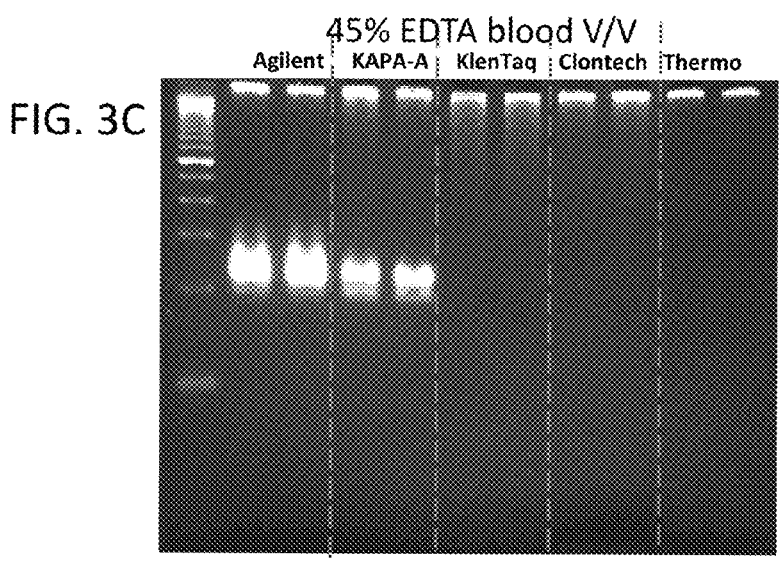
Figure 4A:
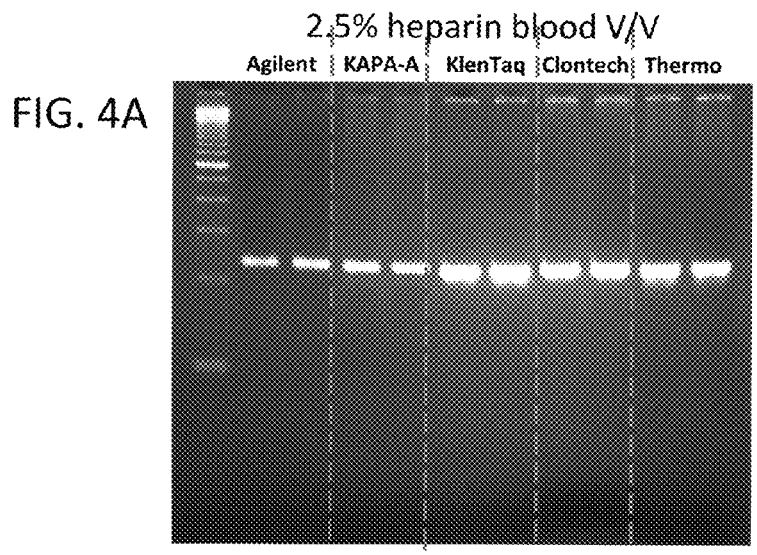
FIG. 4A, FIG. 4B, and FIG. 4C are a set of photographs showing comparison of the activity of Taq mutant 1C2 with those of DNA polymerases from different sources in the presence of heparin-treated whole blood.
Figure 4B:
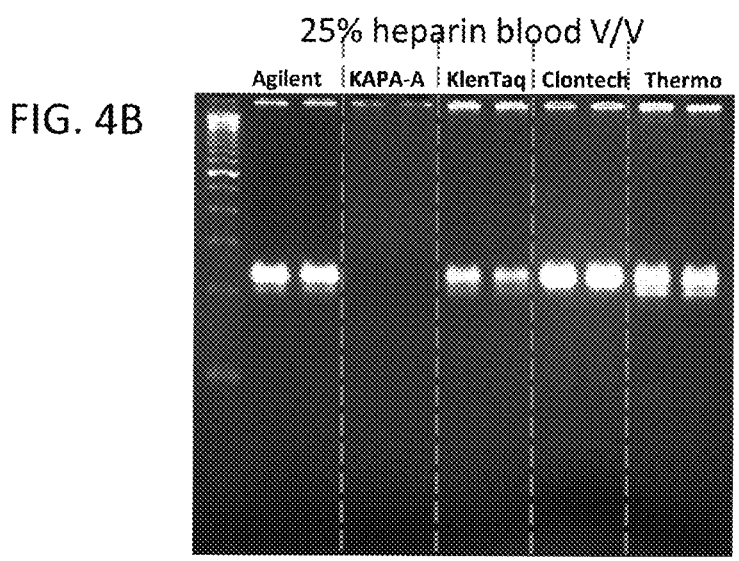
Figure 4C:
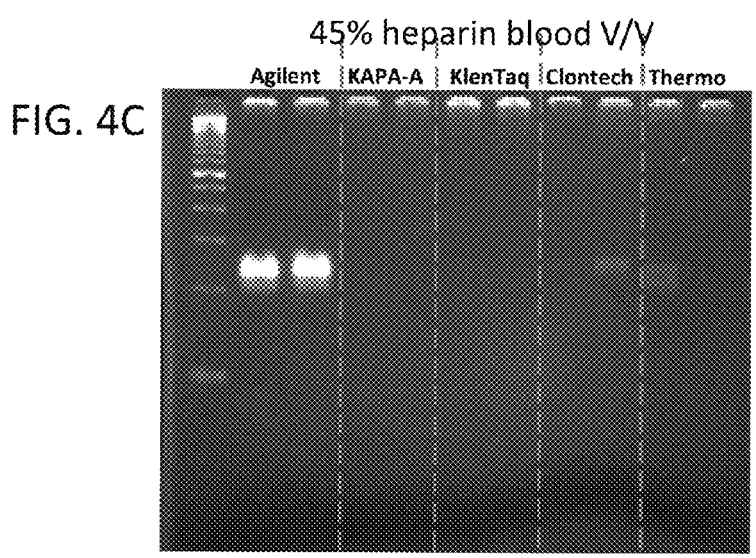

The amplification products were fractionated on a 4% Nusieve agarose gel pre-stained with ethidium bromide. The results are shown in FIGS. 3 and 4, where the sizing ladder was in 100 bp increments, and the same amount of each product (8 μl or 6% of each 50 μl reaction) was loaded onto the gels. These DNA polymerases' resistance to EDTA or heparin are ranked below:

2.5% EDTA blood V/V: Clontech>Agilent>Thermo> KAPA=KlenTaq
25% EDTA blood V/V: Agilent=KlenTaq=Clontech> KAPA>Thermo
45% EDTA blood V/V: Agilent>KAPA (KlenTaq, Clontech, Thermo: no visible product
2.5% heparin blood V/V: KlenTaq>Clontech>Thermo> KAPA>Agilent
25% heparin blood V/V: Clontech>Agilent=Thermo>Klen Taq (KAPA: no visible product)
45% heparin blood V/V: Agilent>>Clontech, Thermo (KlenTaq, Thermo: no visible product)

As shown above, the Taq 1C2 mutant outperformed most of the other polymerases. In addition, it was found that the Taq 1C2 mutant was the only one showing good yields in the presence of 45% v/v of heparinized blood. The Taq 1C2 mutant was also the only one showing good resistance to both EDTA and heparin.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

What is claimed is:

1. An isolated, mutant thermostable Type-A DNA polymerase comprising the amino acid sequence of SEP ID NO: 11, wherein the isolated, mutant thermostable Type-A DNA polymerase possesses (i) DNA polymerase activity and (ii) a higher resistance to a polymerization activity inhibitor than the wild-type DNA polymerase from which the isolated, mutant thermostable Type-A DNA polymerase is derived.

2. The isolated, mutant thermostable Type-A DNA polymerase of claim 1, wherein the polymerization activity inhibitor is an anticoagulant.

3. The isolated, mutant thermostable Type-A DNA polymerase of claim 2, wherein the anticoagulant is EDTA or heparin.

4. The isolated, mutant thermostable Type-A DNA polymerase of claim 1, wherein the isolated, mutant thermostable Type-A DNA polymerase possesses a faster polymerization rate than the wild-type DNA polymerase.

5. A composition comprising (i) the isolated, mutant thermostable Type-A DNA polymerase of claim 1 and (ii) one or more reagents selected from the group consisting of an aqueous buffer, a divalent metal, extension nucleotides, primers, a detergent, a detection agent, and a target nucleic acid.

6. A kit for amplification of a target nucleic acid, the kit comprising (i) the isolated, mutant thermostable Type-A DNA polymerase of claim 1 and (ii) one or more reagents selected from the group consisting of an aqueous buffer, a divalent metal, an extension nucleotide, a primer, a probe, a detergent, a detection agent, a dye, a fluorescent molecule, an anticoagulant, and a cell lysis agent.

7. A method of amplifying a target nucleic acid, the method comprising:
providing a test sample suspected of containing the target nucleic acid;
contacting the test sample with the isolated, mutant thermostable Type-A DNA polymerase of claim 1, a primer that specifically binds to the target nucleic acid, and extension nucleotides to form a mixture, and
incubating the mixture under conditions permitting extension of the primer by the isolated, mutant thermostable Type-A DNA polymerase with the target nucleic acid as a template for incorporation of the extension nucleotides.

8. The method of claim 7, wherein the method is a method of PCR.

9. The method of claim 7, wherein the test sample is a blood sample.

10. The method of claim 9, wherein the mixture contains at least 1% v/v of the blood sample.

11. An isolated nucleic acid comprising a nucleotide sequence that encodes the isolated, mutant thermostable Type-A DNA polymerase of claim 1.

12. The nucleic acid of claim 11, wherein the nucleotide sequence is at least 70% identical to SEQ ID NO: 12.

13. A vector or a host cell comprising the isolated nucleic acid of claim 11.

14. A method of producing a polypeptide, comprising culturing a host cell comprising an isolated nucleic acid comprising a nucleotide sequence that encodes the isolated, mutant thermostable Type-A DNA polymerase of claim 1 in a medium under conditions permitting expression of a polypeptide encoded by the isolated nucleic acid, and purifying the isolated, mutant thermostable Type-A DNA polymerase of claim 1 from the cultured cell or the medium.

* * * * *

UNITED STATES PATENT AND TRADEMARK OFFICE
CERTIFICATE OF CORRECTION

PATENT NO. : 9,758,773 B2  
APPLICATION NO. : 14/568549  
DATED : September 12, 2017  
INVENTOR(S) : Nancy Mckinney et al.

Page 1 of 1

It is certified that error appears in the above-identified patent and that said Letters Patent is hereby corrected as shown below:

In the Specification

In Column 1, Line 27, delete "ire" and insert -- in --, therefor.

In Column 2, Line 60, delete "V1551," and insert -- V155I, --, therefor.

In Column 5, Line 4, delete "V1551," and insert -- V155I, --, therefor.

In the Claims

In Column 71, Line 61, in Claim 1, delete "SEP" and insert -- SEQ --, therefor.

Signed and Sealed this  
Seventh Day of November, 2017

Joseph Matal  
*Performing the Functions and Duties of the*  
*Under Secretary of Commerce for Intellectual Property and*  
*Director of the United States Patent and Trademark Office*